United States Patent
Buntzman

(10) Patent No.: US 10,822,662 B2
(45) Date of Patent: Nov. 3, 2020

(54) DIAGNOSTIC METHODS FOR IDENTIFYING T-CELL LYMPHOMA AND LEUKEMIA BY HIGH-THROUGHPUT TCR-β SEQUENCING

(71) Applicant: Karkinos Precision Oncology LLC, Tucson, AZ (US)

(72) Inventor: Adam Scott Buntzman, Tucson, AZ (US)

(73) Assignee: Karkinos Precision Oncology LLC, Tucson, AZ (US)

( * ) Notice: Subject to any disclaimer, the term of this patent is extended or adjusted under 35 U.S.C. 154(b) by 247 days.

(21) Appl. No.: 15/911,588

(22) Filed: Mar. 5, 2018

(65) Prior Publication Data

US 2018/0258492 A1    Sep. 13, 2018

Related U.S. Application Data

(60) Provisional application No. 62/467,427, filed on Mar. 6, 2017.

(51) Int. Cl.
*C12Q 1/6886* (2018.01)

(52) U.S. Cl.
CPC ...... *C12Q 1/6886* (2013.01); *C12Q 2600/118* (2013.01); *C12Q 2600/156* (2013.01); *C12Q 2600/16* (2013.01)

(58) Field of Classification Search
CPC .................................................. C12Q 1/6886
USPC .......................................................... 506/17
See application file for complete search history.

(56) References Cited

U.S. PATENT DOCUMENTS

| | | | |
|---|---|---|---|
| 5,296,351 A | 3/1994 | Morley et al. | |
| 5,837,447 A | 11/1998 | Gorski | |
| 6,087,096 A | 7/2000 | Dau et al. | |
| 2003/0082591 A1* | 5/2003 | Awrey | C12N 15/90 435/6.13 |
| 2003/0170675 A1* | 9/2003 | Xiang | C12Q 1/6841 435/6.11 |
| 2006/0228714 A1* | 10/2006 | Meyerson | C12N 15/1093 435/6.14 |
| 2006/0234234 A1 | 10/2006 | Van Dongen et al. | |
| 2010/0151471 A1 | 6/2010 | Faham et al. | |
| 2011/0207134 A1 | 8/2011 | Faham et al. | |
| 2012/0172243 A1* | 7/2012 | Davicioni | C12Q 1/6886 506/9 |
| 2015/0307874 A1* | 10/2015 | Jaitin | C12N 15/1096 506/16 |
| 2016/0237487 A1* | 8/2016 | Yu | G16B 20/00 |
| 2016/0362470 A1* | 12/2016 | Johnson | C07K 16/00 |
| 2018/0340167 A1* | 11/2018 | Jakobsen | C07K 14/7051 |

FOREIGN PATENT DOCUMENTS

EP    1544308 B1    1/2009

OTHER PUBLICATIONS

Head et al. (Biotechniques, Feb. 2014, 56: pp. 61-77) (Year: 2014).*
Martinez-Lopez, et al., "Prognostic value of deep sequencing method for minimal residual disease detection in multiple myeloma", Blood, 123(20):3073-9 (May 15, 2014).
Gawad, et al., "Massive evolution of the immunoglobulin heavy chain locus in children with B precursor acute lymphoblastic leukemia", Blood, 120(22):4407-4417 (Nov. 22, 2012).
Van Dongen et al., Leukemia, 17:2257-2317(2003).
Vernau et al.,"T Cell Repertoire Development in XSCID Dogs Following Nonconditioned Allogeneic Bone Marrow Transplantation";Bio Blood Marrow Transplant;13(9):1005-1015 (2007).

* cited by examiner

*Primary Examiner* — Karla A Dines
(74) *Attorney, Agent, or Firm* — Duane Morris LLP

(57) ABSTRACT

A method for diagnosing a lymphoid proliferative disorder (such as lymphoma, T-cell lymphoma or leukemia) in a subject or determining the risk of a subject for a lymphoid proliferative disorder recurrence after transient remission, which includes high throughput T-Cell Receptor β (TCRβ) sequencing tests to identify dominant oncogenic clones in the subject suffering from the lymphoid proliferative disorder. Oligonucleotides primer compositions and kits associated with the above-described methods are also provided herein. Said subject includes living organisms, such as mammals (e.g., dogs, cats, pigs, cows, horses, goats, rabbits, humans), non-mammalian vertebrates, such as birds (e.g., chicken, ducks), fish (e.g., sharks), or frogs, and transgenic species thereof.

25 Claims, 8 Drawing Sheets
Specification includes a Sequence Listing.

SEQUENCE LISTING

```
<160> NUMBER OF SEQ ID NOS: 58

<210> SEQ ID NO 1
<211> LENGTH: 42
<212> TYPE: DNA
<213> ORGANISM: Artificial Sequence
<220> FEATURE:
<223> OTHER INFORMATION: Synthetic primer: Vb primer
<220> FEATURE:
<221> NAME/KEY: misc_feature
<222> LOCATION: (34)..(42)
<223> OTHER INFORMATION: n is a, c, g, or t

<400> SEQUENCE: 1
tcgtcggcag cgtcagatgt gtataagaga cagnnnnnnn nn            42

<210> SEQ ID NO 2
<211> LENGTH: 38
<212> TYPE: DNA
<213> ORGANISM: Artificial Sequence
<220> FEATURE:
<223> OTHER INFORMATION: Synthetic primer: Cbeta primer
<220> FEATURE:
<221> NAME/KEY: misc_feature
<222> LOCATION: (35)..(38)
<223> OTHER INFORMATION: n is a, c, g, or t

<400> SEQUENCE: 2
gtctcgtggg ctcggagatg tgtataagag acagnnnn                 38
```

<210> SEQ ID NO 3
<211> LENGTH: 51
<212> TYPE: DNA
<213> ORGANISM: Artificial Sequence
<220> FEATURE:
<223> OTHER INFORMATION: Synthetic primer: Upstream Primer_N501 barcode

<400> SEQUENCE: 3
aatgatacgg cgaccaccga gatctacact agatcgctcg tcggcagcgt c      51

<210> SEQ ID NO 4
<211> LENGTH: 47
<212> TYPE: DNA
<213> ORGANISM: Artificial Sequence
<220> FEATURE:
<223> OTHER INFORMATION: Synthetic primer: Downstream Primer_N701
      barcode

<400> SEQUENCE: 4
caagcagaag acggcatacg agattcgcct tagtctcgtg ggctcgg            47

<210> SEQ ID NO 5
<211> LENGTH: 66
<212> TYPE: DNA
<213> ORGANISM: Artificial Sequence
<220> FEATURE:
<223> OTHER INFORMATION: Synthetic primer: TRBV3-1(BV6.2)
<220> FEATURE:
<221> NAME/KEY: misc_feature
<222> LOCATION: (34)..(42)
<223> OTHER INFORMATION: n is a, c, g, or t

<400> SEQUENCE: 5
tcgtcggcag cgtcagatgt gtataagaga cagnnnnnnn nntctacttt aatcagggac   60
tcaatc                                                              66

<210> SEQ ID NO 6
<211> LENGTH: 60
<212> TYPE: DNA
<213> ORGANISM: Artificial Sequence
<220> FEATURE:
<223> OTHER INFORMATION: Synthetic primer: TRBV3-2(BV6.1)
<220> FEATURE:
<221> NAME/KEY: misc_feature
<222> LOCATION: (34)..(42)
<223> OTHER INFORMATION: n is a, c, g, or t

<400> SEQUENCE: 6
tcgtcggcag cgtcagatgt gtataagaga cagnnnnnnn nncaacaata aggaactcat   60

<210> SEQ ID NO 7
<211> LENGTH: 62
<212> TYPE: DNA
<213> ORGANISM: Artificial Sequence
<220> FEATURE:
<223> OTHER INFORMATION: Synthetic primer: TRBV5-2(BV2)
<220> FEATURE:
<221> NAME/KEY: misc_feature
<222> LOCATION: (34)..(42)
<223> OTHER INFORMATION: n is a, c, g, or t

<400> SEQUENCE: 7
tcgtcggcag cgtcagatgt gtataagaga cagnnnnnnn nnccagggtc cccggtttct   60
ca                                                                  62

<210> SEQ ID NO 8

```
<211> LENGTH: 60
<212> TYPE: DNA
<213> ORGANISM: Artificial Sequence
<220> FEATURE:
<223> OTHER INFORMATION: Synthetic primer: TRBV5-4(BV18)
<220> FEATURE:
<221> NAME/KEY: misc_feature
<222> LOCATION: (34)..(42)
<223> OTHER INFORMATION: n is a, c, g, or t

<400> SEQUENCE: 8
tcgtcggcag cgtcagatgt gtataagaga cagnnnnnnn nngtctccgc acgattctca     60

<210> SEQ ID NO 9
<211> LENGTH: 61
<212> TYPE: DNA
<213> ORGANISM: Artificial Sequence
<220> FEATURE:
<223> OTHER INFORMATION: Synthetic primer: TRBV7(BV4)
<220> FEATURE:
<221> NAME/KEY: misc_feature
<222> LOCATION: (34)..(42)
<223> OTHER INFORMATION: n is a, c, g, or t

<400> SEQUENCE: 9
tcgtcggcag cgtcagatgt gtataagaga cagnnnnnnn nnagggcccg gagtttctgg     60
t                                                                    61

<210> SEQ ID NO 10
<211> LENGTH: 66
<212> TYPE: DNA
<213> ORGANISM: Artificial Sequence
<220> FEATURE:
<223> OTHER INFORMATION: Synthetic primer: TRBV10(BV13)
<220> FEATURE:
<221> NAME/KEY: misc_feature
<222> LOCATION: (34)..(42)
<223> OTHER INFORMATION: n is a, c, g, or t

<400> SEQUENCE: 10
tcgtcggcag cgtcagatgt gtataagaga cagnnnnnnn nnatgggccg aggctgatct     60
attatt                                                               66

<210> SEQ ID NO 11
<211> LENGTH: 64
<212> TYPE: DNA
<213> ORGANISM: Artificial Sequence
<220> FEATURE:
<223> OTHER INFORMATION: Synthetic primer: TRBV15(BV7)
<220> FEATURE:
<221> NAME/KEY: misc_feature
<222> LOCATION: (34)..(42)
<223> OTHER INFORMATION: n is a, c, g, or t

<400> SEQUENCE: 11
tcgtcggcag cgtcagatgt gtataagaga cagnnnnnnn nngctgctgc tctactacta     60
tgat                                                                 64

<210> SEQ ID NO 12
<211> LENGTH: 61
<212> TYPE: DNA
<213> ORGANISM: Artificial Sequence
<220> FEATURE:
<223> OTHER INFORMATION: Synthetic primer: TRBV16(BV1)
<220> FEATURE:
<221> NAME/KEY: misc_feature
<222> LOCATION: (34)..(42)
<223> OTHER INFORMATION: n is a, c, g, or t
```

<400> SEQUENCE: 12
tcgtcggcag cgtcagatgt gtataagaga cagnnnnnnn nngattttta gccttctgtc    60
c                                                                  61

<210> SEQ ID NO 13
<211> LENGTH: 66
<212> TYPE: DNA
<213> ORGANISM: Artificial Sequence
<220> FEATURE:
<223> OTHER INFORMATION: Synthetic primer: TRBV18(BV10)
<220> FEATURE:
<221> NAME/KEY: misc_feature
<222> LOCATION: (34)..(42)
<223> OTHER INFORMATION: n is a, c, g, or t

<400> SEQUENCE: 13
tcgtcggcag cgtcagatgt gtataagaga cagnnnnnnn nnagccccga gaaaggacac    60
agttat                                                             66

<210> SEQ ID NO 14
<211> LENGTH: 62
<212> TYPE: DNA
<213> ORGANISM: Artificial Sequence
<220> FEATURE:
<223> OTHER INFORMATION: Synthetic primer: TRBV25(BV17)
<220> FEATURE:
<221> NAME/KEY: misc_feature
<222> LOCATION: (34)..(42)
<223> OTHER INFORMATION: n is a, c, g, or t

<400> SEQUENCE: 14
tcgtcggcag cgtcagatgt gtataagaga cagnnnnnnn nnagtctacc agcctctcac    60
ag                                                                 62

<210> SEQ ID NO 15
<211> LENGTH: 66
<212> TYPE: DNA
<213> ORGANISM: Artificial Sequence
<220> FEATURE:
<223> OTHER INFORMATION: Synthetic primer: TRBV26(BV16)
<220> FEATURE:
<221> NAME/KEY: misc_feature
<222> LOCATION: (34)..(42)
<223> OTHER INFORMATION: n is a, c, g, or t

<400> SEQUENCE: 15
tcgtcggcag cgtcagatgt gtataagaga cagnnnnnnn nntttgggct acagctgatc    60
tactac                                                             66

<210> SEQ ID NO 16
<211> LENGTH: 66
<212> TYPE: DNA
<213> ORGANISM: Artificial Sequence
<220> FEATURE:
<223> OTHER INFORMATION: Synthetic primer: TRBV28(BV9)
<220> FEATURE:
<221> NAME/KEY: misc_feature
<222> LOCATION: (34)..(42)
<223> OTHER INFORMATION: n is a, c, g, or t

<400> SEQUENCE: 16
tcgtcggcag cgtcagatgt gtataagaga cagnnnnnnn nnggctgctc tactggtcct    60
ataata                                                             66

```
<210> SEQ ID NO 17
<211> LENGTH: 67
<212> TYPE: DNA
<213> ORGANISM: Artificial Sequence
<220> FEATURE:
<223> OTHER INFORMATION: Synthetic primer: TRBV1
<220> FEATURE:
<221> NAME/KEY: misc_feature
<222> LOCATION: (34)..(42)
<223> OTHER INFORMATION: n is a, c, g, or t

<400> SEQUENCE: 17
tcgtcggcag cgtcagatgt gtataagaga cagnnnnnnn nngccccggg gacgaggagc      60
tcgtatc                                                               67

<210> SEQ ID NO 18
<211> LENGTH: 63
<212> TYPE: DNA
<213> ORGANISM: Artificial Sequence
<220> FEATURE:
<223> OTHER INFORMATION: Synthetic primer: TRBV4
<220> FEATURE:
<221> NAME/KEY: misc_feature
<222> LOCATION: (34)..(42)
<223> OTHER INFORMATION: n is a, c, g, or t

<400> SEQUENCE: 18
tcgtcggcag cgtcagatgt gtataagaga cagnnnnnnn nnggagagtg accctcaact      60
gtg                                                                   63

<210> SEQ ID NO 19
<211> LENGTH: 62
<212> TYPE: DNA
<213> ORGANISM: Artificial Sequence
<220> FEATURE:
<223> OTHER INFORMATION: Synthetic primer: TRBV12-2
<220> FEATURE:
<221> NAME/KEY: misc_feature
<222> LOCATION: (34)..(42)
<223> OTHER INFORMATION: n is a, c, g, or t

<400> SEQUENCE: 19
tcgtcggcag cgtcagatgt gtataagaga cagnnnnnnn nntcctgtgg attactcggg      60
ga                                                                    62

<210> SEQ ID NO 20
<211> LENGTH: 62
<212> TYPE: DNA
<213> ORGANISM: Artificial Sequence
<220> FEATURE:
<223> OTHER INFORMATION: Synthetic primer: TRBV20
<220> FEATURE:
<221> NAME/KEY: misc_feature
<222> LOCATION: (34)..(42)
<223> OTHER INFORMATION: n is a, c, g, or t

<400> SEQUENCE: 20
tcgtcggcag cgtcagatgt gtataagaga cagnnnnnnn nngtgacctc taacgtgggc      60
aa                                                                    62

<210> SEQ ID NO 21
<211> LENGTH: 62
<212> TYPE: DNA
<213> ORGANISM: Artificial Sequence
<220> FEATURE:
<223> OTHER INFORMATION: Synthetic primer: TRBV22
```

```
<220> FEATURE:
<221> NAME/KEY: misc_feature
<222> LOCATION: (34)..(42)
<223> OTHER INFORMATION: n is a, c, g, or t

<400> SEQUENCE: 21
tcgtcggcag cgtcagatgt gtataagaga cagnnnnnnn nnggtctgcg gctgatttac    60
ct                                                                  62

<210> SEQ ID NO 22
<211> LENGTH: 62
<212> TYPE: DNA
<213> ORGANISM: Artificial Sequence
<220> FEATURE:
<223> OTHER INFORMATION: Synthetic primer: TRBV24
<220> FEATURE:
<221> NAME/KEY: misc_feature
<222> LOCATION: (34)..(42)
<223> OTHER INFORMATION: n is a, c, g, or t

<400> SEQUENCE: 22
tcgtcggcag cgtcagatgt gtataagaga cagnnnnnnn nncttctcga acggacctgg    60
ag                                                                  62

<210> SEQ ID NO 23
<211> LENGTH: 62
<212> TYPE: DNA
<213> ORGANISM: Artificial Sequence
<220> FEATURE:
<223> OTHER INFORMATION: Synthetic primer: TRBV27
<220> FEATURE:
<221> NAME/KEY: misc_feature
<222> LOCATION: (34)..(42)
<223> OTHER INFORMATION: n is a, c, g, or t

<400> SEQUENCE: 23
tcgtcggcag cgtcagatgt gtataagaga cagnnnnnnn nngaaccgcg acgctatgta    60
ct                                                                  62

<210> SEQ ID NO 24
<211> LENGTH: 64
<212> TYPE: DNA
<213> ORGANISM: Artificial Sequence
<220> FEATURE:
<223> OTHER INFORMATION: Synthetic primer: TRBV29
<220> FEATURE:
<221> NAME/KEY: misc_feature
<222> LOCATION: (34)..(42)
<223> OTHER INFORMATION: n is a, c, g, or t

<400> SEQUENCE: 24
tcgtcggcag cgtcagatgt gtataagaga cagnnnnnnn nntgcagagg ccacctacga    60
aagt                                                                64

<210> SEQ ID NO 25
<211> LENGTH: 62
<212> TYPE: DNA
<213> ORGANISM: Artificial Sequence
<220> FEATURE:
<223> OTHER INFORMATION: Synthetic primer: TRBV30
<220> FEATURE:
<221> NAME/KEY: misc_feature
<222> LOCATION: (34)..(42)
<223> OTHER INFORMATION: n is a, c, g, or t

<400> SEQUENCE: 25
```

```
tcgtcggcag cgtcagatgt gtataagaga cagnnnnnnn nntgagacac cgcacaactt    60
ca                                                                   62
```

<210> SEQ ID NO 26
<211> LENGTH: 59
<212> TYPE: DNA
<213> ORGANISM: Artificial Sequence
<220> FEATURE:
<223> OTHER INFORMATION: Synthetic primer: NewBC
<220> FEATURE:
<221> NAME/KEY: misc_feature
<222> LOCATION: (35)..(38)
<223> OTHER INFORMATION: n is a, c, g, or t

<400> SEQUENCE: 26

```
gtctcgtggg ctcggagatg tgtataagag acagnnnntc tctgcttctg atggttcaa     59
```

<210> SEQ ID NO 27
<211> LENGTH: 57
<212> TYPE: DNA
<213> ORGANISM: Artificial Sequence
<220> FEATURE:
<223> OTHER INFORMATION: Synthetic primer: TRBV3-1(BV6.2)

<400> SEQUENCE: 27

```
tcgtcggcag cgtcagatgt gtataagaga cagtctactt taatcaggga ctcaatc       57
```

<210> SEQ ID NO 28
<211> LENGTH: 51
<212> TYPE: DNA
<213> ORGANISM: Artificial Sequence
<220> FEATURE:
<223> OTHER INFORMATION: Synthetic primer: TRBV3-2(BV6.1)

<400> SEQUENCE: 28

```
tcgtcggcag cgtcagatgt gtataagaga cagcaacaat aaggaactca t              51
```

<210> SEQ ID NO 29
<211> LENGTH: 53
<212> TYPE: DNA
<213> ORGANISM: Artificial Sequence
<220> FEATURE:
<223> OTHER INFORMATION: Synthetic primer: TRBV5-2(BV2)

<400> SEQUENCE: 29

```
tcgtcggcag cgtcagatgt gtataagaga cagccagggt ccccggtttc tca            53
```

<210> SEQ ID NO 30
<211> LENGTH: 51
<212> TYPE: DNA
<213> ORGANISM: Artificial Sequence
<220> FEATURE:
<223> OTHER INFORMATION: Synthetic primer: TRBV5-4(BV18)

<400> SEQUENCE: 30

```
tcgtcggcag cgtcagatgt gtataagaga caggtctccg cacgattctc a              51
```

<210> SEQ ID NO 31
<211> LENGTH: 52
<212> TYPE: DNA
<213> ORGANISM: Artificial Sequence
<220> FEATURE:
<223> OTHER INFORMATION: Synthetic primer: TRBV7(BV4)

<400> SEQUENCE: 31

```
tcgtcggcag cgtcagatgt gtataagaga cagagggccc ggagtttctg gt             52
```

<210> SEQ ID NO 32
<211> LENGTH: 57
<212> TYPE: DNA
<213> ORGANISM: Artificial Sequence
<220> FEATURE:
<223> OTHER INFORMATION: Synthetic primer: TRBV10(BV13)

<400> SEQUENCE: 32
tcgtcggcag cgtcagatgt gtataagaga cagatgggcc gaggctgatc tattatt      57

<210> SEQ ID NO 33
<211> LENGTH: 55
<212> TYPE: DNA
<213> ORGANISM: Artificial Sequence
<220> FEATURE:
<223> OTHER INFORMATION: Synthetic primer: TRBV15(BV7)

<400> SEQUENCE: 33
tcgtcggcag cgtcagatgt gtataagaga caggctgctg ctctactact atgat        55

<210> SEQ ID NO 34
<211> LENGTH: 52
<212> TYPE: DNA
<213> ORGANISM: Artificial Sequence
<220> FEATURE:
<223> OTHER INFORMATION: Synthetic primer: TRBV16(BV1)

<400> SEQUENCE: 34
tcgtcggcag cgtcagatgt gtataagaga caggattttt agccttctgt cc           52

<210> SEQ ID NO 35
<211> LENGTH: 57
<212> TYPE: DNA
<213> ORGANISM: Artificial Sequence
<220> FEATURE:
<223> OTHER INFORMATION: Synthetic primer: TRBV18(BV10)

<400> SEQUENCE: 35
tcgtcggcag cgtcagatgt gtataagaga cagagccccg agaaaggaca cagttat      57

<210> SEQ ID NO 36
<211> LENGTH: 53
<212> TYPE: DNA
<213> ORGANISM: Artificial Sequence
<220> FEATURE:
<223> OTHER INFORMATION: Synthetic primer: TRBV25(BV17)

<400> SEQUENCE: 36
tcgtcggcag cgtcagatgt gtataagaga cagagtctac cagcctctca cag          53

<210> SEQ ID NO 37
<211> LENGTH: 57
<212> TYPE: DNA
<213> ORGANISM: Artificial Sequence
<220> FEATURE:
<223> OTHER INFORMATION: Synthetic primer: TRBV26(BV16)

<400> SEQUENCE: 37
tcgtcggcag cgtcagatgt gtataagaga cagtttgggc tacagctgat ctactac      57

<210> SEQ ID NO 38
<211> LENGTH: 57
<212> TYPE: DNA
<213> ORGANISM: Artificial Sequence
<220> FEATURE:

<223> OTHER INFORMATION: Synthetic primer: TRBV28(BV9)

<400> SEQUENCE: 38
tcgtcggcag cgtcagatgt gtataagaga cagggctgct ctactggtcc tataata        57

<210> SEQ ID NO 39
<211> LENGTH: 58
<212> TYPE: DNA
<213> ORGANISM: Artificial Sequence
<220> FEATURE:
<223> OTHER INFORMATION: Synthetic primer: TRBV1

<400> SEQUENCE: 39
tcgtcggcag cgtcagatgt gtataagaga caggccccgg ggacgaggag ctcgtatc       58

<210> SEQ ID NO 40
<211> LENGTH: 54
<212> TYPE: DNA
<213> ORGANISM: Artificial Sequence
<220> FEATURE:
<223> OTHER INFORMATION: Synthetic primer: TRBV4

<400> SEQUENCE: 40
tcgtcggcag cgtcagatgt gtataagaga cagggagagt gaccctcaac tgtg           54

<210> SEQ ID NO 41
<211> LENGTH: 53
<212> TYPE: DNA
<213> ORGANISM: Artificial Sequence
<220> FEATURE:
<223> OTHER INFORMATION: Synthetic primer: TRBV12-2

<400> SEQUENCE: 41
tcgtcggcag cgtcagatgt gtataagaga cagtcctgtg gattactcgg gga            53

<210> SEQ ID NO 42
<211> LENGTH: 53
<212> TYPE: DNA
<213> ORGANISM: Artificial Sequence
<220> FEATURE:
<223> OTHER INFORMATION: Synthetic primer: TRBV20

<400> SEQUENCE: 42
tcgtcggcag cgtcagatgt gtataagaga caggtgacct ctaacgtggg caa            53

<210> SEQ ID NO 43
<211> LENGTH: 53
<212> TYPE: DNA
<213> ORGANISM: Artificial Sequence
<220> FEATURE:
<223> OTHER INFORMATION: Synthetic primer: TRBV22

<400> SEQUENCE: 43
tcgtcggcag cgtcagatgt gtataagaga cagggtctgc ggctgattta cct            53

<210> SEQ ID NO 44
<211> LENGTH: 53
<212> TYPE: DNA
<213> ORGANISM: Artificial Sequence
<220> FEATURE:
<223> OTHER INFORMATION: Synthetic primer: TRBV24

<400> SEQUENCE: 44
tcgtcggcag cgtcagatgt gtataagaga cagcttctcg aacggacctg gag            53

```
<210> SEQ ID NO 45
<211> LENGTH: 53
<212> TYPE: DNA
<213> ORGANISM: Artificial Sequence
<220> FEATURE:
<223> OTHER INFORMATION: Synthetic primer: TRBV27

<400> SEQUENCE: 45
tcgtcggcag cgtcagatgt gtataagaga caggaaccgc gacgctatgt act          53

<210> SEQ ID NO 46
<211> LENGTH: 55
<212> TYPE: DNA
<213> ORGANISM: Artificial Sequence
<220> FEATURE:
<223> OTHER INFORMATION: Synthetic primer: TRBV29

<400> SEQUENCE: 46
tcgtcggcag cgtcagatgt gtataagaga cagtgcagag gccacctacg aaagt        55

<210> SEQ ID NO 47
<211> LENGTH: 53
<212> TYPE: DNA
<213> ORGANISM: Artificial Sequence
<220> FEATURE:
<223> OTHER INFORMATION: Synthetic primer: TRBV30

<400> SEQUENCE: 47
tcgtcggcag cgtcagatgt gtataagaga cagtgagaca ccgcacaact tca          53

<210> SEQ ID NO 48
<211> LENGTH: 55
<212> TYPE: DNA
<213> ORGANISM: Artificial Sequence
<220> FEATURE:
<223> OTHER INFORMATION: Synthetic primer: NewBC

<400> SEQUENCE: 48
gtctcgtggg ctcggagatg tgtataagag acagtctctg cttctgatgg ttcaa        55

<210> SEQ ID NO 49
<211> LENGTH: 51
<212> TYPE: DNA
<213> ORGANISM: Artificial Sequence
<220> FEATURE:
<223> OTHER INFORMATION: Synthetic primer: N501

<400> SEQUENCE: 49
aatgatacgg cgaccaccga gatctacact agatcgctcg tcggcagcgt c            51

<210> SEQ ID NO 50
<211> LENGTH: 52
<212> TYPE: DNA
<213> ORGANISM: Artificial Sequence
<220> FEATURE:
<223> OTHER INFORMATION: Synthetic primer: N502

<400> SEQUENCE: 50
aatgatacgg cgaccaccga gatctacacc tctctatctc gtcggcagcg tc           52

<210> SEQ ID NO 51
<211> LENGTH: 52
<212> TYPE: DNA
<213> ORGANISM: Artificial Sequence
<220> FEATURE:
<223> OTHER INFORMATION: Synthetic primer: N503
```

<400> SEQUENCE: 51
aatgatacgg cgaccaccga gatctacact atcctctctc gtcggcagcg tc        52

<210> SEQ ID NO 52
<211> LENGTH: 52
<212> TYPE: DNA
<213> ORGANISM: Artificial Sequence
<220> FEATURE:
<223> OTHER INFORMATION: Synthetic primer: N504

<400> SEQUENCE: 52
aatgatacgg cgaccaccga gatctacaca gagtagactc gtcggcagcg tc        52

<210> SEQ ID NO 53
<211> LENGTH: 47
<212> TYPE: DNA
<213> ORGANISM: Artificial Sequence
<220> FEATURE:
<223> OTHER INFORMATION: Synthetic primer: N701

<400> SEQUENCE: 53
caagcagaag acggcatacg agattcgcct tagtctcgtg ggctcgg             47

<210> SEQ ID NO 54
<211> LENGTH: 47
<212> TYPE: DNA
<213> ORGANISM: Artificial Sequence
<220> FEATURE:
<223> OTHER INFORMATION: Synthetic primer: N702

<400> SEQUENCE: 54
caagcagaag acggcatacg agatctagta cggtctcgtg ggctcgg             47

<210> SEQ ID NO 55
<211> LENGTH: 47
<212> TYPE: DNA
<213> ORGANISM: Artificial Sequence
<220> FEATURE:
<223> OTHER INFORMATION: Synthetic primer: N703

<400> SEQUENCE: 55
caagcagaag acggcatacg agatttctgc ctgtctcgtg ggctcgg             47

<210> SEQ ID NO 56
<211> LENGTH: 47
<212> TYPE: DNA
<213> ORGANISM: Artificial Sequence
<220> FEATURE:
<223> OTHER INFORMATION: Synthetic primer: N704

<400> SEQUENCE: 56
caagcagaag acggcatacg agatgctcag gagtctcgtg ggctcgg             47

<210> SEQ ID NO 57
<211> LENGTH: 55
<212> TYPE: DNA
<213> ORGANISM: Artificial Sequence
<220> FEATURE:
<223> OTHER INFORMATION: Synthetic primer: New Cb

<400> SEQUENCE: 57
gtctcgtggg ctcggagatg tgtataagag acagtctctg cttctgatgg ttcaa    55

<210> SEQ ID NO 58
<211> LENGTH: 59

```
<212> TYPE: DNA
<213> ORGANISM: Artificial Sequence
<220> FEATURE:
<223> OTHER INFORMATION: Synthetic primer: Cb Molecular Tagged Primer
<220> FEATURE:
<221> NAME/KEY: misc_feature
<222> LOCATION: (35)..(38)
<223> OTHER INFORMATION: n is a, c, g, or t

<400> SEQUENCE: 58
gtctcgtggg ctcggagatg tgtataagag acagnnnntc tctgcttctg atggttcaa      59
```

DIAGNOSTIC METHODS FOR IDENTIFYING T-CELL LYMPHOMA AND LEUKEMIA BY HIGH-THROUGHPUT TCR-β SEQUENCING

CROSS-REFERENCE TO RELATED APPLICATIONS

This utility application claims priority to and the benefit of U.S. Ser. No. 62/467,427, filed Mar. 6, 2017, which is incorporated by reference herein in its entirety.

FIELD

The present invention relates to methods for diagnosing or determining the risk of a lymphoid proliferative disorder (such as lymphoma, T-cell lymphoma and leukemia) in a subject. More particularly, the invention relates to novel high throughput T-Cell Receptor β (TCRβ) sequencing tests to identify dominant oncogenic clones in lymphoma or leukemia patients or subjects. Such patients or subjects include living organisms, such as mammals (e.g., dogs, cats, pigs, cows, horses, goats, rabbits, humans), non-mammalian jawed vertebrates, such as birds (e.g., chicken, ducks), jawed fish (e.g., sharks), or frogs, and transgenic species thereof.

BACKGROUND

The following discussion of the background of the invention is merely provided to aid the reader in understanding the invention and is not admitted to describe or constitute prior art to the present invention.

The number of deaths due to canine lymphoid malignancies range from 67,000-300,000 deaths per year within the population of approximately 80 million US dogs. Not only is the incidence high in pets, the mortality statistics are grim. Canine lymphoma patients typically initially respond extremely well to the same chemotherapeutic regimen used in human patients (e.g., CHOPS, L-asparaginase, etc.), with remission rates exceeding 90%. However, the remission time is short and relapse of the tumor is the norm. The 9 month-1 year survival rate is under 50% with treatment, and most dogs eventually succumb to the tumor. The major survival impediment from canine lymphoid malignancy is recurrence after transient remission. A similar scenario existed in human lymphoid cases in the 1960s, but human lymphoid cancer 5-year survival rates have climbed since then (4.2 fold for leukemia, 2.2 fold for lymphoma), due to improved diagnostics and treatment regimen. Veterinary oncologists remain hampered in their management of patients by the lack of sensitive diagnostic tools, especially tests that monitor minimal residual disease like high throughput immune receptor sequencing. The absence of sensitive and cost effective minimally invasive diagnostic tests in veterinary oncology is certain to continue to contribute to the poor prognosis of canine lymphoid cancers.

In humans, 12%-15% of non-Hodgkin's lymphoma's (NHL) are of T-cell origin. However, in dogs the proportion of T-cell NHL tumor cases is higher than in humans, and is increasing in incidence. Indeed, recent evidence suggests that the frequency of T-cell lymphoma in dogs is 32.8% of lymphoma cases. Other reports have indicated over 40% of cases are of T-cell origin, which may be reflective of breed specific differences in the ratios of T-cell to B-cell tumors. While Basset Hound lymphomas present with T-cell markers at a rate of only 5.6%, an extreme example of a breed disparity in lymphoid tumors presenting with a T cell phenotype exist in Boxers and Irish Wolfhounds where it approaches 85% and 100% respectively. Various breeds of Shepherds, Spaniels, and Terriers, as well as Huskies, and Golden Retrievers also have high proportion of tumors with a T-cell phenotype (53.6%-88.9%). In addition, 73% of all chronic lymphocytic leukemia (CLL) cases have a T-cell phenotype. The prevalence of T-cell lymphoma and leukemia in popular breeds necessitates the development of TCR-based diagnostic tests.

Therefore, there is a need for sensitive, cost-effective and minimally invasive diagnostic tests in veterinary oncology to evaluate the presence of minimal residual disease and contribute to the poor prognosis of lymphoid cancers, particularly T-cell lymphoma and leukemia in mammals, including canines.

BRIEF SUMMARY

In consideration of the above problems, the present invention is based on the discovery of a novel method that utilizes high throughput T cell receptor beta chain (TCRβ) sequencing to provide sensitive tests for diagnosing and determining the risk of lymphoid proliferative disorders, including but not limited to lymphoma, T-cell lymphoma and leukemia, in a subject.

In one exemplary embodiment, a method for diagnosing a lymphoid proliferative disorder in a subject suspected of having a lymphoid proliferative disorder comprising the steps of (i) creating a TCRβ DNA library using a biological sample obtained from the subject, (ii) assessing the frequency of each TCR clonotype; (iii) identifying a tumor-bearing TCR clonotype using one or more clonal abundance indices; (iv) comparing the frequency of the tumor-bearing TCR clonotype to an abundance threshold criterion derived from the frequency of the dominant clone in samples obtained from a plurality of subjects diagnosed as not having a lymphoid proliferative disorder; and (v) identifying the subject as having a lymphoid proliferative disorder when the frequency is above the abundance threshold criterion or identifying the subject as not having a lymphoid proliferative disorder or a decreased likelihood of recurrence when the frequency is below the abundance threshold criterion. In further exemplary embodiment, the lymphoid proliferative disorder is lymphoma, T-cell lymphoma or leukemia.

In further exemplary embodiment, the biological sample and the samples each comprises lymph node tissue, peripheral blood lymphocytes, bone marrow, gut associated lymphoid tissue, or any other tissue with a malignant lymphoid lesion, or a combination thereof. In a further exemplary embodiment, the creation of the TCRβ DNA library comprises the steps of: (i) isolating RNA from the biological sample; (ii) generating DNA product via reverse transcription of the RNA and amplifying resultant DNA product; (iii) analyzing the amplified DNA products; and (iv) sequencing of the amplified DNA product. The steps of reverse transcription and amplification, can, in some exemplary embodiments, be performed using RT-PCR. The analysis of the amplified DNA products may, in further exemplary embodiments, be performed by agarose gel electrophoresis. In yet further exemplary embodiments, the sequencing of the amplified DNA product is performed using high-throughput sequencing using a sequencer (such as Illumina MiSeq Instrument or the like) utilizing at least 2×250 bp chemistry.

In another exemplary embodiment, the abundance threshold criterion can be greater than or equal to 1%, 2%, 3%, 4%, 5%, 10%, or 15%. The abundance threshold criterion in a further exemplary embodiment is greater than or equal to 5%. The step of amplification of resultant DNA product can, in some exemplary embodiments, comprise incorporating a molecular tag into each molecule of input TCR. Such a molecular tag can be, in some exemplary embodiments, a randomized molecular tag, and the incorporation of such a tag can, in some exemplary embodiments, comprise the step of annealing each molecule of input TCR mRNA to a primer having a molecular tag. In further exemplary embodiments, such a primer has a nucleic acid sequence comprising one or more of SEQ ID NO. 1 through SEQ ID NO. 58. In even further exemplary embodiments, a primer has a nucleic acid sequence comprising one or more of SEQ ID NO. 5 through SEQ ID NO. 25. In even further exemplary embodiments, a primer has a nucleic acid sequence comprising one or more of SEQ ID NO. 5 through SEQ ID NO. 25. SEQ ID NO. 5 through SEQ ID NO. 25 can be found in TABLE 1 below.

In another exemplary embodiment, a method for determining the risk of a subject for T-cell lymphoma or leukemia recurrence after transient remission comprising the steps of: (i) creating a TCRβ DNA library using a biological sample obtained from the subject, (ii) assessing the frequency of each TCR clonotype; (iii) identifying a tumor-bearing TCR clonotype using one or more clonal abundance indices; (iv) comparing the frequency of the tumor-bearing TCR clonotype to an abundance threshold criterion derived from the frequency of the dominant clone in samples obtained from a plurality of subjects diagnosed as not having T-cell lymphoma; and (v) identifying the subject as having an increased likelihood of T-cell lymphoma or leukemia recurrence when the frequency is above the abundance threshold criterion or identifying the subject as having a decreased likelihood of recurrence when the frequency is below the abundance threshold criterion.

In an exemplary embodiment, the biological sample and the samples each comprises lymph node tissue, peripheral blood lymphocytes, bone marrow, gut associated lymphoid tissue, or any other tissue with a malignant lymphoid lesion, or a combination thereof. In further exemplary embodiments, the creation of the TCRβ DNA library comprises the steps of: (i) isolating RNA from the biological sample; (ii) generating DNA product via reverse transcription of the RNA and amplifying the resultant DNA product; (iii) analyzing the amplified DNA products; and (iv) sequencing of the amplified DNA product. The steps of reverse transcription and amplification, can, in some exemplary embodiments, be performed using RT-PCR. The analysis of the amplified DNA products can, in further exemplary embodiments, be performed by agarose gel electrophoresis. In yet further exemplary embodiments, the sequencing of the amplified DNA product is performed using high-throughput sequencing using a sequencer (such as Illumina MiSeq Instrument or the like) utilizing at least 2×250 bp chemistry.

In an exemplary embodiment, the abundance threshold criterion may be greater than or equal to 1%, 2%, 3%, 4%, 5%, 10%, or 15%. The abundance threshold criterion in a further exemplary embodiment is greater than or equal to 5%. The step of amplification of the resultant DNA product can, in some exemplary embodiments, comprise incorporating a molecular tag into each molecule of input TCR. Such a molecular tag can be, in some exemplary embodiments, a randomized molecular tag, and the incorporation of such a tag can, in some exemplary embodiments, comprise the step of annealing each molecule of input TCR mRNA to a primer having a molecular tag. In further exemplary embodiments, such a primer has a nucleic acid sequence comprising one or more of SEQ ID NO. 1 through SEQ ID NO. 58, or, in even further exemplary embodiments, a nucleic acid sequence comprising one or more of SEQ ID NO. 5 through SEQ ID NO. 25. The primer can also have a nucleic acid sequence comprising one or more of SEQ ID NO. 16 through SEQ ID NO. 25.

In yet another exemplary embodiment, a kit for diagnosing a canine subject suspected to be suffering from or susceptible to recurring canine T-cell lymphoma, said kit comprising at least one forward primer and at least one reverse primer, the forward primer and the reverse primer each has a nucleic acid sequence comprising one or more of SEQ ID NO.1 through SEQ ID NO. 58, together with instructions for carrying out the methods described above.

In yet another exemplary embodiment, a kit for diagnosing a subject suspected to be suffering from or susceptible to recurring T-cell lymphoma or leukemia, said kit comprising at least one forward primer and at least one reverse primer, the forward primer and the reverse primer each has a nucleic acid sequence comprising one or more of SEQ ID NO.1 through SEQ ID NO. 58, together with instructions for carrying out the method discussed above.

In yet another exemplary embodiment, a kit for determining the risk of a subject for T-cell lymphoma or leukemia recurrence after transient remission comprising at least one forward primer and at least one reverse primer, the forward primer and the reverse primer each has a nucleic acid sequence comprising one or more of SEQ ID NO.1 through SEQ ID NO. 58, together with instructions for carrying out the method discussed above.

In yet another exemplary embodiment, an oligonucleotide primer composition comprising at least 15 and not more than 100 contiguous nucleotide of a V or C region encoding gene sequence for TCRβ, wherein the composition has a sequence selected from the group consisting of SEQ ID NO. 16 through SEQ ID NO. 25.

As used herein, "clonotype" means a recombined nucleotide sequence encoding a T cell receptor (TCR) or a portion thereof. As used herein, "clonotype profile" or "repertoire profile" is a tabulation of clonotypes of a sample of T cells (such as, for example, a peripheral blood sample containing such T cells) that includes all or substantially all of the repertoire's clonotypes and their relative abundances. In some exemplary embodiments of the invention, clonotypes comprise portions of a TCRβ chain.

As used herein, "repertoire" or "immune repertoire" means a set of distinct recombined nucleotide sequences that encode TCRβs or fragments thereof in a population of lymphocytes of an individual, wherein the nucleotide sequences of the set have a correspondence with distinct lymphocytes or their clonal subpopulations for all or substantially all of the lymphocytes of the population. In one exemplary embodiment, a population of lymphocytes from which a repertoire is determined is taken from one or more tissue samples, such as one or more blood samples, lymph node, skin or tumor mass. A member nucleotide sequence of a repertoire is referred to herein as a "clonotype".

"Sequence tag" (or "tag") means an oligonucleotide that is attached to a polynucleotide or template and is used to identify and/or track the polynucleotide or template in a reaction. An "oligonucleotide tag" can be attached to the 3'- or 5'-end of a polynucleotide or template or it may be inserted into the interior of such polynucleotide or template to form a linear conjugate, sometimes referred to herein as a "tagged polynucleotide," or "tagged template."

As used herein, the term "nucleic acid molecule" or "nucleic acid" refer to an oligonucleotide, nucleotide or polynucleotide. A nucleic acid molecule can include deoxyribonucleotides, ribonucleotides, modified nucleotides, or nucleotide analogs in any combination.

As used herein, the term "nucleotide" refers to a chemical moiety having a sugar (modified, unmodified, or an analog thereof), a nucleotide base (modified, unmodified, or an analog thereof), and a phosphate group (modified, unmodified, or an analog thereof). Nucleotides include deoxyribonucleotides, ribonucleotides, and modified nucleotide analogs including, for example, locked nucleic acids (LNAs), peptide nucleic acids (PNAs), L-nucleotides, ethylene-bridged nucleic acids (ENAs), arabinoside, and nucleotide analogs (including abasic nucleotides).

As used herein, "primer" refers to an oligonucleotide, synthetic or naturally occurring, which is capable of acting as a point of initiation of nucleic acid synthesis or replication along a template strand when placed under conditions in which the synthesis of a substantially complementary strand is catalyzed by a polymerase. Within the context of reverse transcription, primers are composed of nucleic acids and prime on RNA templates. Within the context of PCR, primers are composed of nucleic acids and prime on DNA templates.

As used herein, the term "substantially complementary" is meant that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target sequence, positioned 3' or 5' to a contiguous sequence of bases that hybridize under stringent hybridization conditions to a target sequence.

As used herein, "amplification" is meant one or more methods known in the art for copying a target nucleic acid, thereby increasing the number of copies of a selected nucleic acid sequence. Amplification may be exponential or linear. A target nucleic acid may be either genomic DNA or RNA. The sequences amplified in this manner form an "amplicon."

As used herein, "biological sample" or "sample" is meant a sample obtained from a biological source. When obtained from a subject (e.g., a canine patient), a biological sample may, by way of non-limiting example, consist of or comprise blood, serum, plasma, cerebrospinal fluid (CSF), urine, feces, tissue samples including biopsy samples (e.g., obtained by a fine needle aspirate (FNA) or excisional biopsy), and those obtained by non-invasive techniques such as epidermal samples (e.g., cheek swabs), amniotic fluid, bone marrow sample and/or chorionic villi. The term "biological sample" or "sample" includes samples which have been processed to release or otherwise make available a nucleic acid for sequencing as described herein. For example, a "biological sample" or "sample" can include a cDNA that has been obtained by reverse transcription of RNA from cells in a biological sample. As used herein, "subject" or "individual" or "patient" can include living organisms, such as mammals (e.g., dogs, cats, pigs, cows, horses, goats, rabbits, humans), non-mammalian vertebrates, such as birds (e.g., chicken, ducks), fish (e.g., sharks), or frogs, and transgenic species thereof.

As used herein, sequences that are "substantially identical" to each other have identical nucleotides at least at about 50% of aligned nucleotide positions, preferably at least at about 75%, 85%, or 95% of aligned nucleotide positions, and more preferably at least at about 99% of aligned nucleotide positions.

BRIEF DESCRIPTION OF THE FIGURES

The accompanying drawings, which are incorporated herein and form a part of the specification, illustrates the embodiments of the present invention and, together with the description, further serve to explain the principles of the embodiments and to enable a person skilled in the pertinent art to make and use the embodiments. The drawings are for illustration purposes only and are not necessarily drawn to scale.

FIG. 4(D) shows the broad distribution of the T cells from the healthy donor over the entire landscape. FIG. 4(A)-(C) show that the tumor clone in the respective canine lymphoma patients appears to have displaced the normal TCR repertoire.

DETAILED DESCRIPTION

For purposes of the description hereinafter, it is to be understood that the exemplary embodiments described below may assume alternative variations and embodiments. It is also to be understood that the specific articles, compositions, methods and/or processes described herein are exemplary and should not be considered as limiting.

The present invention is directed to the use of high throughput TCRβ sequencing in diagnosing or determining the risk of a lymphoid proliferative disorder (such as lymphoma, leukemia, canine T-cell lymphoma) in a subject.

Figure 1:
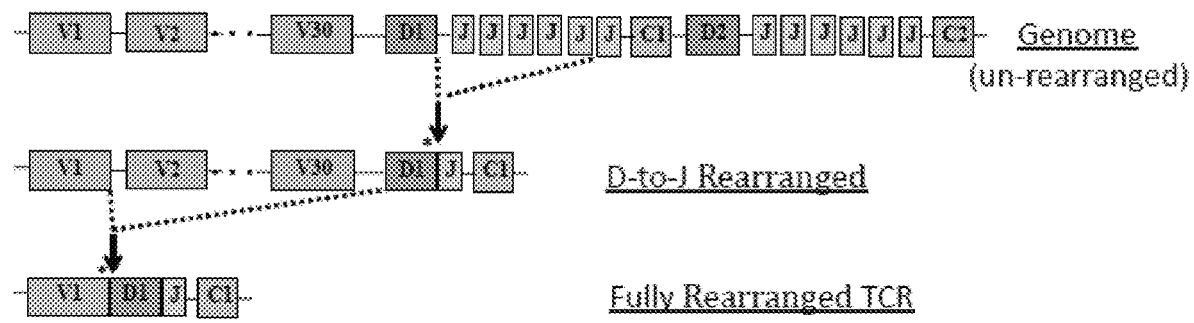
FIG. 1 is an illustration of the V(D)J recombination process for the TCR β chain, including the steps of deletion of nucleotides, extension of palindromic "p-nucleotides", and the addition of "n-nucleotides" at the junctions between the V, D, and J gene fragments.

Lymphocytes (T-cells and B-cells) are critical to the effective function of the adaptive immune system. As each lymphocyte develops, it generates an immune receptor (T-Cell Receptor or Antibody) that can detect a microbe during an infection. To create immune receptors, lymphocytes go through a complex process of gene rearrangement called V(D)J Recombination. The genes that code for T-cell receptors (TCR) and antibodies (Ab) are initially segmented into Variable (V), Diversity (D) and Joining (J) gene fragments on chromosome 16 of the dog genome, resulting in non-functional genes in most cells of the body. However, as each lymphocyte matures, its genome is enzymatically cut and spliced to bring the fragments together to form a functional TCR gene in T-cells or Ab gene in B-cells, as shown schematically in FIG. 1. The enzymes of the V(D)J Recombination system (e.g. Rag, TdT, Artemis, etc) ensure the creation of a diverse population of lymphocytes, each with a potentially unique receptor, by modifying the termini of the gene fragments during the recombination process. DNA is deleted or palindromic nucleotides are extended (p-nucleotides) by the exonuclease activity of the Artemis enzyme complex and additional DNA (n-nucleotides) are added by the Terminal Deoxynucleotidyl Transferase (TdT) enzyme. The potential for diversity in the V(D)J recombination system is enormous; exceeding $10^{15}$ (thousands of trillions) different immune receptors in T-cells alone. Each lymphocyte, with its novel receptor, has the potential to interact with a different set of microbes. This receptor diversity is the very reason that the adaptive immune system of all jawed vertebrates can detect an astonishing array of infections and protect against microbes that the host has never had a prior exposure to.

The sequence of immune receptors (TCR or Ab) also provide clinicians and researchers with ideal clonal biomarkers for tracking the status of the adaptive immune system during infections, vaccination, recovery from stem cell transplantation, inflammation and during autoimmune syndromes. The sequence of immune receptors can also be used to identify when the immune system malfunctions, as occurs in lymphoid cancers (e.g., lymphoma, leukemia, myeloma). When a lymphocyte undergoes oncogenic transformation and then proceeds to replicate, the immune receptor sequence now represents a unique clonal biomarker of the initial cancer cell and all of its cellular progeny. The immune receptor sequence becomes a signature of that tumor cell as the number of neoplastic cells expands in the patient and distinguishes the cancer cells from the remaining healthy lymphocytes. As the lymphoid tumor progresses, it becomes a progressively larger proportion of the repertoire of immune receptors in the individual. At peak clinical burden, the tumor clone can represent over 90% of the lymphocytes isolated from the patient's tissue sample, functionally "crowding out" the healthy cells. As a patient is successfully treated (e.g., ablation, chemotherapy, radiation, stem cell transplantation, or immunomodulation) the percentage of the tumor clone can plummet until unobservable by classical techniques (e.g., histology, flow cytometry, PCR/spectratyping, imaging).

Provided herein are methods for diagnosing T-cell lymphoma in a canine subject suspected of having T-cell lymphoma or leukemia or for determining the risk of a subject for T-cell lymphoma or leukemia recurrence after transient remission by: (i) creating a TCRβ DNA library using a biological sample obtained from the subject, (ii) assessing the frequency of each clonotype; (iii) identifying a tumor-bearing TCR clonotype using clonal abundance indices; (iv) comparing the frequency of the tumor-bearing TCR clonotype to an abundance threshold criterion derived from the frequency of the dominant clone in samples obtained from subjects diagnosed as not having T-cell lymphoma or leukemia; and (v) identifying the subject as having T-cell lymphoma or leukemia or increased likelihood of T-cell lymphoma or leukemia recurrence when the frequency is above the abundance threshold criterion or identifying the subject as not having T-cell lymphoma or leukemia or a decreased likelihood of recurrence when the frequency is below the abundance threshold criterion. Methods of determining the risk of relapse may also be performed by creating a TCRβ DNA library of a T-cell lymphoma or leukemia patient, determining the tumor-bearing TCR clonotype, and then testing specifically for that clonotype during remission. If the determined tumor-bearing TCR clonotype is above the abundance threshold criterion, then the subject has increased chance of relapse. Continued observation of the tumor clone during clinical remission is defined as "Minimal Residual Disease".

Amplification of Nucleic Acid Populations

Amplicons of target populations of nucleic acids may be generated by a variety of amplification techniques. In one exemplary embodiment of the present invention, multiplex PCR is used to amplify members of a mixture of nucleic acids, particularly mixtures comprising TCRb or portions thereof. Guidance for carrying out multiplex PCRs of such immune molecules is found in the following references, which are incorporated herein by reference in their entirety: Morley, U.S. Pat. No. 5,296,351; Gorski, U.S. Pat. No. 5,837,447; Dau, U.S. Pat. No. 6,087,096; Von Dongen et al, U.S. Patent Application Publication No. 2006/0234234; European Patent Application Publication No. EP 1544308B1; and the like. The foregoing references describe the technique referred to as "spectratyping," where a population of immune molecules are amplified by multiplex PCR after which the sequences of the resulting amplicon are physically separated, e.g., by electrophoresis, in order to determine whether there is a predominant size class. Such a class would indicate a predominant clonal population of lymphocytes that, in turn, would be indicative of the disease state. In spectratyping, it is important to select primers that display little or no cross-reactivity (i.e., that do not anneal to binding sites of other primers); otherwise there may be a false representation of size classes in the amplicon. In the present invention, so long as the nucleic acids of a population are uniformly amplified, cross-reactivity of primers is permissible because the sequences of the amplified nucleic acids are analyzed in the present invention, not merely their sizes. As described more fully below, in one exemplary embodiment, the step of spatially isolating individual nucleic acid molecules is achieved by carrying out a primary multiplex amplification of a preselected target sequence using forward and reverse primers that each have tails non-complementary to the target sequences to produce a first amplicon whose member sequences have common sequences at each end that allow further manipulation. For example, such common ends may include primer binding sites for continued amplification using just a single forward primer and a single reverse primer instead of multiples of each, or for bridge amplification of individual molecules on a solid surface, or the like. Such common ends may be added in a single amplification as described above, or they may be added in a two-step procedure to avoid difficulties associated with manufacturing and exercising quality control over mixtures of long primers (e.g., 50-70 bases or more). In such a two-step process (described more fully in Example 1 below) the primary amplification is carried out as described above, except that the primer tails are limited in length to provide only forward and reverse primer binding sites at the ends of the sequences of the first amplicon. A secondary amplification is then carried out using secondary amplification primers specific to these primer binding sites to add further sequences to the ends of a second amplicon. The secondary amplification primers have tails non-complementary to the target sequences, which form the ends of the second amplicon and which may be used in connection with sequencing the clonotypes of the second amplicon. In some exemplary embodiments, such added sequences may include primer binding sites for generating sequence reads and primer binding sites for carrying out bridge PCR on a solid surface to generate clonal populations of spatially isolated individual molecules.

In addition to ensuring that the sample contains sufficient cells to be representative of the original sample, it is important that the amplicons generated by the multiplex PCR reaction be representative of the cells in the reaction. In order to achieve this, primer conditions should be selected such that amplification from every cell in the reaction occurs.

TCR sequences or portions thereof can be amplified from nucleic acid in a multiplex reaction using at least one primer that anneals to the C region and one or more primers that can anneal to one or more V segments. The number of primers that anneal to V segments in a multiplex reaction can be, for example, at least 1, 5, 10, 15, 20, 25, 30, 35, 40, 45, 50, 55, 60, 65, 70, 75, 80, 90, 100, 120, or 130. Where there is a canine subject, the number can, in some exemplary embodiments, be between about 1 and about 23. The number of primers that anneal to V segments in a multiplex reaction can be, for example, 10-60, 20-50, 30-50, 40-50, 20-40, 30-40, or 35-40. The primers can anneal to different V segments. Amplification of TCR genes can, in some exemplary embodiments, occur as described in Example 1.

The TCR or sequence can, in some exemplary embodiments of the invention, be amplified using a primary amplification step and a secondary amplification step. Each of the different amplification steps can comprise different primers. The different primers can introduce sequences not originally present in the immune gene sequence. For example, the amplification procedure can add new primer binding sites to the ends of the target sequences to convert a multiplex amplification to a singleplex amplification or the amplification procedure can add one or more tags to the 5' and/or 3' end of amplified TCR sequence. The tag can be a sequence that facilitates subsequent sequencing of the amplified DNA. The tag can be a sequence that facilitates binding the amplified sequence to a solid support.

Other means of amplifying nucleic acids can be used in the methods of the provided invention include. These include, for example, reverse transcription-PCR, real-time PCR, quantitative real-time PCR, digital PCR (dPCR), digital emulsion PCR (dePCR), clonal PCR, amplified fragment length polymorphism PCR (AFLP PCR), allele specific PCR, assembly PCR, asymmetric PCR, colony PCR, helicase-dependent amplification (HDA), Hot Start PCR, inverse PCR (IPCR), in situ PCR long PCR (extension of DNA greater than about 5 kilobases), multiplex PCR, nested PCR (uses more than one pair of primers), single-cell PCR, touchdown PCR, loop-mediated isothermal PCR (LAMP), and nucleic acid sequence based amplification (NASBA).

Other amplification schemes include: Ligase Chain Reaction, Branch DNA Amplification, Rolling Circle Amplification. Circle to Circle Amplification, SPIA amplification, Target Amplification by Capture and Ligation (TACL) amplification, and RACE amplification.

The information in RNA in a sample can also, in some exemplary embodiments, be converted to cDNA by using reverse transcription. PolyA primers, random primers, and/or gene specific primers can be used in reverse transcription reactions in accordance with conventional protocols.

Nucleic Acid Processing

After amplification of DNA from the genome (or amplification of nucleic acid in the form of cDNA by reverse transcribing RNA), the individual nucleic acid molecules can be isolated, optionally re-amplified, and then sequenced individually. Exemplary amplification protocols may be found in van Dongen et al. Leukemia, 17: 2257-2317 (2003) or van Dongen et al, U.S. Patent Application Publication No. 2006/0234234, which is incorporated herein by reference in their entirety. Polymerases that can be used for amplification in the methods of the invention are commercially available and include, for example. Taq polymerase, AccuPrime polymerase, or Pfu. The choice of polymerase to use can be based on whether fidelity or efficiency is preferred.

Amplification bias may be avoided by carrying out a two-stage amplification wherein a small number of amplification cycles are implemented in a first, or primary, stage using primers having tails non-complementary with the target sequences. The tails include primer binding sites that are added to the ends of the sequences of the primary amplicon so that such sites are used in a second stage amplification using only a single forward primer and a single reverse primer, thereby eliminating a primary cause of amplification bias. Preferably, the primary PCR will have a small enough number of cycles (e.g., 2-10) to minimize the differential amplification by the different primers. The secondary amplification is done with one pair of primers and hence the issue of differential amplification is minimal.

High-Throughput Sequencing

Any high-throughput technique for sequencing nucleic acids can be used in the method of the invention. DNA sequencing techniques include dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. In an exemplary embodiment, high throughput sequencing on the Illumina Miseq platform can be performed.

Constructing Clonotypes

Methods for constructing clonotypes from sequence read data are known in the art, and are taught by, for example, e.g. Faham and Willis, U.S. Patent Application Publication Nos. 2010/0151471 and 2011/0207134, which are incorporated herein by reference in their entirety. Briefly, constructing clonotypes from sequence read data depends in part on the sequencing method used to generate such data, as the different methods have different expected read lengths and data quality. In one approach, a Solexa sequencer is employed to generate sequence read data for analysis. In exemplary embodiments, FASTQ output sequence files are generated during sequencing, and are then informatically un-binned according to the unique barcodes utilized to differentiate each donor sample. They can then be matched to the reference germ-line canine TCR variable and joining (V and J) gene sequences derived from a repository. In exemplary embodiments, the forward and reverse read for each sequence derived from the FASTQ MiSeq output file is consensus called using the highest Illumina quality score (Qual) to clarify disparate nucleotides on each read. For canine subjects, the consensus sequence can then be compared to 23 germline reference V-gene segment sequences to identify the V-gene usage for each sequence and to define the partition of the 5'-end of the Complementarity Determining Region #3 (CDR3 region) (=the Cysteine codon motif). The experimental sequence can, in some exemplary embodiments, then be matched to 13 germline reference J-genes to identify the J-gene usage for each sequence and to define the partition of the 3'-end of the CDR3 region (=PGxG=Phenylalanine-Glycine-Any Amino Acid-Glycine motif). The matching of each experimental sequence to the reference V-gene and J-gene segments can be accomplished by maximum homology (BLAST or Smith-Waterman algorithm) or by exact identity alignment. The length of the CDR3 region is determined to be in-frame, if the CDR3 length is divisible by 3 evenly. All sequences with ambiguous nucleotides (N) or stop-codons within the CDR3 are excluded.

EXAMPLES

The present methods, thus generally described, will be understood more readily by reference to the following examples, which are provided by way of illustration and are not intended to be limiting of the present methods and kits.

Example 1: Creation of TCRβ Library

Method A:

Lymph node samples were obtained from 4 dogs (3 canine T-cell lymphoma patients & 1 healthy donor patient) that were being evaluated. Lymph node tissue was homogenized and an extraction was performed to isolate total RNA in Trizol reagent according to the manufacturer's instructions. Reverse transcription was performed on the lymph node RNA with Superscript III Reverse Transcriptase according to the manufacturers instruction at 50 degrees C. for 45 minutes (random hexamers). Polymerase chain reaction (PCR) was performed with Taq polymerase with primers annealing to the constant region of the TCRβ chain and each variable gene region, coupled to Illumina MiSeq adaptor sequences (for example, SEQ ID NOS. 1 & 2). The DNA PCR amplification products were analyzed by agarose gel electrophoresis, and extracted by Qiagen gel extraction. The Vb amplicons from each patient were then amplified in a secondary PCR reaction to incorporate 4 unique bar codes (to informatically differentiate each patient sample) and additional Illumina adaptors (for example, SEQ ID NOS. 49-56). The DNA library PCR amplification products were again analyzed by agarose gel electrophoresis, and the final TCRβ DNA products were again gel purified as above. As quality control to confirm the size and purity of the TCRβ library, the TCRβ DNA libraries from each patient were analyzed on an Agilent Bioanalyzer chip (i.e., the Agilent DNA 1000 chip kit). An on-a-chip capillary electrophoresis bioanalyzing product or kit or a high sensitivity small fragment analysis kit (such as any High Sensitivity Small Fragment Analysis Kit by Advanced Analytical Technologies Inc. ("AATI"), including High Sensitivity Small Fragment Analysis Kit #DNF-477) and the like can also be used herein. The samples underwent high throughput sequencing on the Illumina MiSeq platform, and were processed through an informatics pipeline to identify sequences with errors within the germline regions and to enumerate the frequency of observation of each TCR clone sequences within the population of T-cells in the lymph node, including the tumor clonotype. The informatics pipeline processes each of the millions of sequences derived from the Illumina MiSeq instrument and identifies the TRBV gene and TRBJ gene that represents the V(D)J recombinant that was in each T-cell. The TRBV gene and TRBJ genes in each sequence is identified by maximum homology to the germline DNA for each of those genes. PCR and sequencing errors in the germline DNA regions can be determined by comparison with reference sequences and by evaluating the Illumina quality scores for each nucleotide, in addition to identifying the variation of each sequence that contains the same molecular tag and the same barcode. The "complementarity determining region #3"" (CDR3) of the T-cell receptor is identified as the DNA in between anchor residues of the TRBV and TRBJ genes, represented by the cysteine codon in the TRBV gene and the "PGxG" motif in the TRBJ gene. Each unique V(D)J recombinant sequence can be quantified within each clinical sample based on the frequency that the sequence appears in the Illumina MiSeq files.

The FASTQ output sequence files were informatically un-binned according to the unique barcodes utilized to differentiate each donor sample, and then matched to the reference germ-line canine TCR variable and joining (V and J) gene sequences derived from the IMGT repository. All TCR sequences with ambiguous nucleotide calls, reported as "N", within the critical CDR3 region and the flanking germline segments were culled from the dataset, as were sequences that had mutations or sequencing errors that placed the TCR out-of-frame (indels) or that contained an in-frame stop-codon. The frequency of each unique clonotype was enumerated to identify the tumor bearing TCR clonotype by clonal abundance indices (5%) when normalized per million TCR sequences. The clonal abundance index is the proportion of the tumor sequence relative to the non-tumor sequences in the dataset, expressed as a percentage.

Method B:

In order to minimize PCR amplification bias and enable culling of any sequencing errors, an alternative method may be used to create the TCR library from the patient samples.

In the alternative method, lymph node tissue or peripheral blood lymphocytes would be homogenized and an extraction performed to isolate total RNA (or genomic DNA) in Trizol reagent according to the manufacturer's instructions. If mRNA is utilized as a template, reverse transcription is performed on the RNA with Superscript III Reverse Transcriptase according to the manufacturers instruction at 50 degrees C. for 45 minutes (Cb primer). After reverse transcription of TCR mRNA into first strand cDNA, a 2-round Polymerase chain reaction (PCR) method is performed, with primers that anneal to all known functional canine TCR Variable (V) β gene segments as well as the Constant β domain.

Twelve of the Vb primers (SEQ ID NOs. 5-15) were derived from Vernau et al., "T Cell Repertoire Development in XSCID Dogs Following Nonconditioned Allogeneic Bone Marrow Transplantation", Biology of Blood and Marrow Transplantation, Vol. 13(9): 1005-1015 (2007), which is incorporated herein by reference in its entirety, and nine new Vb primers (SEQ ID NOs. 16-25) and a new Cb primer (SEQ ID NOs. 57-58) were designed to amplify all known canine Vb genes. Molecular tagged versions of the primers can also be utilized according to methods known to those of skill in the art. The primers used for the purposes of this example and their corresponding sequences are shown below in Table 1.

Primer design was performed in an iterative process of optimizing the predicted melting temperature (Tm), delta G of the binding of the primer to the template, minimizing the presence of primer homo-dimmers and hetero-dimmers as well as mono-molecular primer hairpins, optimizing GC-richness, minimizing repeat structure, and minimizing the complementarity to other loci in the genome, while retaining a annealing length of the primers to 10-25 bases. For the purposes of this example only, there was an attempt to choose primers with a Tm in the range of 50-65 C, without homopolymer stretches or areas of self-complementarity or cross-complementarity with other primers in the primer set. Other variables and ranges may be selected for using methods known to those of skill in the art. Multiple web-based programs were utilized to evaluate these paramaters for each new primer, including Primer3-Plus, IDT OligoAnalyzer, and the UCSC Dog In-Silico PCR tool. The efficacy of the primers was tested under scaled PCR conditions (varying anneling temp, extension time, magnesium concentration, primer and template concentrations, presence of amplification adjuncts like DMF, DMSO, trimethyl-glycine, glycerol, etc). Any other suitable primer design method known by those of skill in the art may be used. For the purposes of this example, a Cb primer having the sequence (SEQ ID NO. 57)
GTCTCGTGGGCTCGGAGATGTGTATAAGAGACAGTCTCTGCTTCTGATGG

TTCAA and a corresponding Cb molecular tagged primer having the sequence (SEQ ID NO. 58)
GTCTCGTGGGCTCGGAGATGTGTATAAGAGACAGNNNNTCTCTGCTTCTG

ATGGTTCA were developed using the methods described above.

TABLE 1

| Vb Primer Name: | Sequence: | SEQ ID NO: |
|---|---|---|
| TRBV3-1 | TCGTCGGCAGCGTCAGATGTGTATAAGAGACAG NNNNNNNNNNTCTACTTTAATCAGGGACTCAATC | 5 |
| TRBV3-2 | TCGTCGGCAGCGTCAGATGTGTATAAGAGACAG NNNNNNNNNNCAACAATAAGGAACTCAT | 6 |
| TRBV5-2 | TCGTCGGCAGCGTCAGATGTGTATAAGAGACAG NNNNNNNNNNCCAGGGTCCCCGGTTTCTCA | 7 |
| TRBV5-4 | TCGTCGGCAGCGTCAGATGTGTATAAGAGACAG NNNNNNNNNNGTCTCCGCACGATTCTCA | 8 |
| TRBV7 | TCGTCGGCAGCGTCAGATGTGTATAAGAGACAG NNNNNNNNNNAGGGCCCGGAGTTTCTGGT | 9 |
| TRBV10 | TCGTCGGCAGCGTCAGATGTGTATAAGAGACAG NNNNNNNNNNATGGGCCGAGGCTGATCTATTATT | 10 |

TABLE 1-continued

| Vb Primer Name: | Sequence: | SEQ ID NO: |
|---|---|---|
| TRBV15 | TCGTCGGCAGCGTCAGATGTGTATAAGAGACAG NNNNNNNNNNGCTGCTGCTCTACTACTATGAT | 11 |
| TRBV16 | TCGTCGGCAGCGTCAGATGTGTATAAGAGACAG GNNNNNNNNNATTTTTAGCCTTCTGTCC | 12 |
| TRBV18 | TCGTCGGCAGCGTCAGATGTGTATAAGAGACAG NNNNNNNNNNAGCCCCGAGAAAGGACACAGTTAT | 13 |
| TRBV25 | TCGTCGGCAGCGTCAGATGTGTATAAGAGACAG NNNNNNNNNNAGTCTACCAGCCTCTCACAG | 14 |
| TRBV26 | TCGTCGGCAGCGTCAGATGTGTATAAGAGACAG NNNNNNNNNNTTTGGGCTACAGCTGATCTACTAC | 15 |
| TRBV28 | TCGTCGGCAGCGTCAGATGTGTATAAGAGACAG NNNNNNNNNNGGCTGCTCTACTGGTCCTATAATA | 16 |
| TRBV1 | TCGTCGGCAGCGTCAGATGTGTATAAGAGACAG NNNNNNNNNNGCCCCGGGGACGAGGAGCTCGTATC | 17 |
| TRBV4 | TCGTCGGCAGCGTCAGATGTGTATAAGAGACAG GNNNNNNNNNGAGAGTGACCCTCAACTGTG | 18 |
| TRBV12-2 | TCGTCGGCAGCGTCAGATGTGTATAAGAGACAG NNNNNNNNNNTCCTGTGGATTACTCGGGGA | 19 |
| TRBV20 | TCGTCGGCAGCGTCAGATGTGTATAAGAGACAG NNNNNNNNNNGTGACCTCTAACGTGGGCAA | 20 |
| TRBV22 | TCGTCGGCAGCGTCAGATGTGTATAAGAGACAG NNNNNNNNNNGGTCTGCGGCTGATTTACCT | 21 |
| TRBV24 | TCGTCGGCAGCGTCAGATGTGTATAAGAGACAG CNNNNNNNNNNTTCTCGAACGGACCTGGAG | 22 |
| TRBV27 | TCGTCGGCAGCGTCAGATGTGTATAAGAGACAG NNNNNNNNNNGAACCGCGACGCTATGTACT | 23 |
| TRBV29 | TCGTCGGCAGCGTCAGATGTGTATAAGAGACAG NNNNNNNNNNTGCAGAGGCCACCTACGAAAGT | 24 |
| TRBV30 | TCGTCGGCAGCGTCAGATGTGTATAAGAGACAG NNNNNNNNNNTGAGACACCGCACAACTTCA | 25 |

The initial PCR reaction consists of only two rounds of amplification, to ensure that only one molecular tag is incorporated into each molecule of input TCR and to limit the differential amplification bias classically caused by logarithmic amplification in multiplexed PCR reactions. The primers in the initial "2-round PCR reaction" contain oligonucleotides on the 5' end of each primer that enable a second nested amplification by incorporating: (1) sequencing platform oligonucleotides (available from Illumina, San Diego, Calif.); and (2) Randomized Molecular tags on each end of the amplicon (A, T, C, and G nucleotides are randomly incorporated at each of the 10-15 nucleotides).

During the initial 2 rounds of PCR, each molecule of TCR mRNA is appended with a unique molecular tag which will propagate from the single-molecule template through the logarithmic PCR amplification of the next PCR reaction. After the first 2-round amplification, the DNA template is purified from residual primers with AMPure magnetic beads. The primers for the second nested PCR reaction contain the following elements: (1) TRUSEQ and NEXTERA (Illumina) oligonucleotide sequences; and (2) Illumina barcodes to differentiate each sample that may be admixed and run on a single high throughput sequencing chip.

The second PCR reaction is performed with common Illumina oligonucleotides that flank the molecular tag region. The primer characteristics enable tagging of each sample and each input mRNA within each sample, thus allowing for identification of residual PCR amplification biases and normalization of such biases as well as de-binning of admixed samples. The molecular tagging approach incorporates nucleotides into the forward and reverse primers to create 268+ million molecular tag variants. The outcome sequences can be normalized per initial input TCR molecule in the sample, by computationally assessing each unique molecular tag. After agarose gel purification, the purity and size distribution of the TCR library is confirmed with an Agilent Bioanalyzer to confirm the removal of residual primers. Additional size selection and purification of the TCR β library can be performed by agarose gel electrophoresis or by utilizing a Pippin Prep apparatus (Sage Science). The quantity of each TCR library were then determined by real time PCR and sequenced on an Illumina MiSeq Instrument utilizing the 2×250 bp chemistry. Alternative sequencing platforms that may be utilized are Illumina HiSeq2500, Roche 454, or Ion Torrent PGM/Proton instrument.

Reduced clustering density and staggered offset can be used to compensate for the repetitive constant region of the TCR and excessively narrowed repertoire that may occur in cancer patients. A series of plasmid encoded cTCRβ sequences are used as spike-in controls to confirm the minimal biasing of the pipeline and to enumerate the total sequencing error for each experiment.

Example 2: Determination of Canine Tumor TCRβ Clonotype

The TCR library was created and sequenced as described in Example 1, Method A above. As shown in Table 2 below, over 8 million valid canine TCR sequence reads, encoding 180,866 unique clonotypes, were obtained from the 4 samples. Table 1 shows the sequence frequencies and unique nucleotypes from the three lymphoma patients and one healthy donor patient. Over 1 million sequences were obtained from each individual, and the overall mean sequencing depth of these samples exceeded 44.5× coverage.

TABLE 2

|  | Patient 1 | Patient 2 | Patient 3 | Healthy Donor | Total |
| --- | --- | --- | --- | --- | --- |
| # Valid Sequences | 2,433,505 | 1,005,696 | 2,830,509 | 1,791,207 | 8,060,817 |
| # Valid Nucleotypes | 13,316 | 21,981 | 58,071 | 87,498 | 180,866 |

Figure 2:
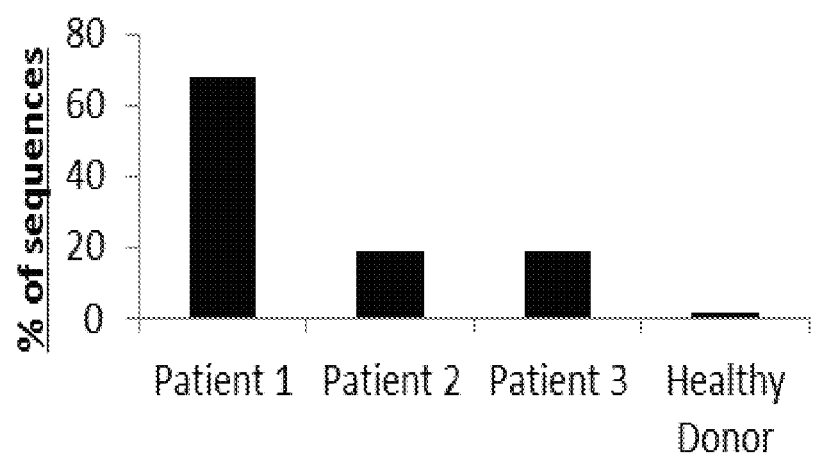
FIG. 2 is a bar graph showing the dominant tumor T-cell receptor clone burden, as a percentage of all sequences observed in the specific patient. Patients 1-3 are three lymphoma canine patients and the Healthy Donor represents one healthy donor canine patient. The frequency of the high abundance TCR clone observed within a patient's sample is divided by the total frequency of all of the TCR clones observed in that sample and then multiplied by 100 to derive the dominant clone's percentage of all sequences observed in the sample from that patient. For example, in Patient 1, the percent of sequences=(1,656,218/2,433,505)×100.

As expected, the TCR repertoire of the healthy donor patient was extremely diverse, and no single TCRβ clone exceeded 1.59% of all of the total TCR sequences in that individual. However, in the 3 lymphoma patients the dominant (highest frequency) clone represented 68%, 18.7%, and 19% of all sequences within the respective patients repertoire, as shown in FIG. 2. Table 3 indicates the absolute frequency of the dominant clone from each dog. Notably, the high frequency tumor clone within patient #1 was observed 1,656,218 times out of a total of 2,433,505 sequences isolated from that individual, an example of extreme clonal abundance.

TABLE 3

|  | Patient 1 | Patient 2 | Patient 3 | Healthy Donor |
| --- | --- | --- | --- | --- |
| Frequency of dominant clone | 1,656,218 | 188,709 | 536,514 | 28,650 |

The sequences of the V-gene, J-gene, and CDR3 of the dominant TCR clones in each individual are shown in Table 4 below.

TABLE 4

| Patient 1 | TRBV25, TRBJ1~2, GCCAGCAGTGAAAATACAGGTTTTTTAAC (SEQ ID NO. 59) |
| --- | --- |
| Patient 2 | TRBV25, TRBJ1~1, GCCAGCAGTGGGCGGGGTACAGGCTGGGAAGTGTTC (SEQ ID NO. 60) |
| Patient 3 | TRBV5~2, TRBJ2~5, GCCAGCAGCACGTACGAGGAGGGGGCGAATACCCAGTAC (SEQ ID NO. 61) |
| Healthy Donor Patient | TRBV24, TRBJ1~1, GCCAGCAGCGATTCGGGGGAATACACTGAAGTGTTC (SEQ ID NO. 62) |

Figure 3:
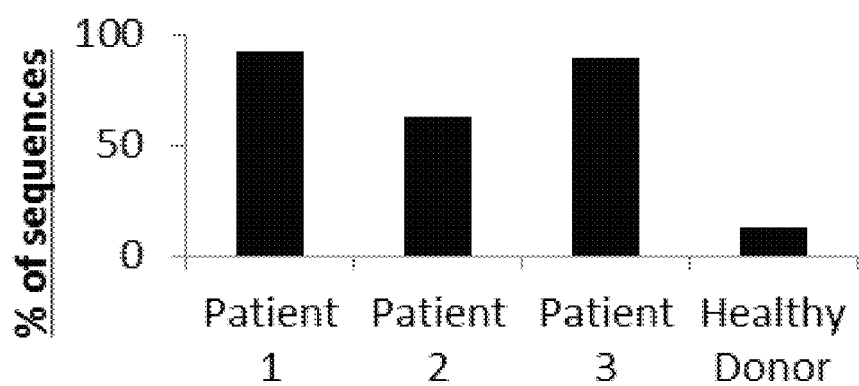
FIG. 3 is a bar graph showing the dominant tumor T-cell receptor clone burden, as a percentage of sequences expressing the same V-gene as the tumor. Patients 1-3 are three lymphoma canine patients and the Healthy Donor represents one healthy donor canine patient. The frequency of the high abundance TCR clone observed within a patient's sample is divided by the total frequency of all of the TCR clones observed in that sample that share the same V-gene and then multiplied by 100 to derive the dominant clone's percentage of all sequences observed in the sample from that patient. For example, in Patient 1, the percent of TRBV25+sequences=(1,656,218/1,796,486)×100=92.19%.
Figure 4A:
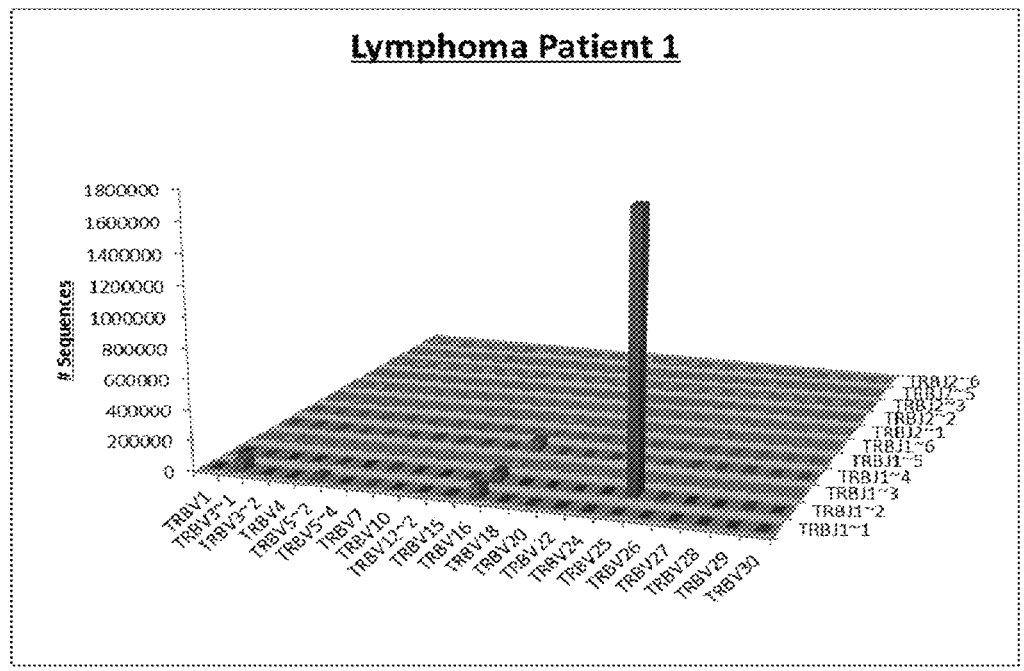
FIGS. 4(A)-(D) are bar graphs showing the V/J gene repertoire landscape and frequency profiling for V-genes and J-genes.
Figure 4B:
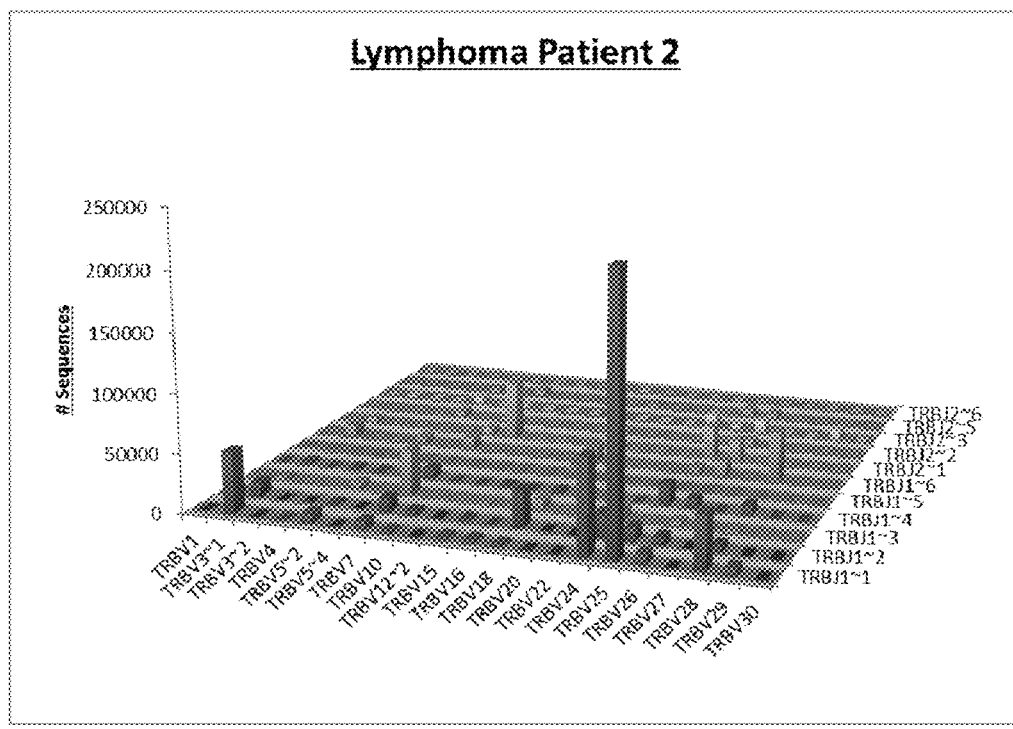
Figure 4C:
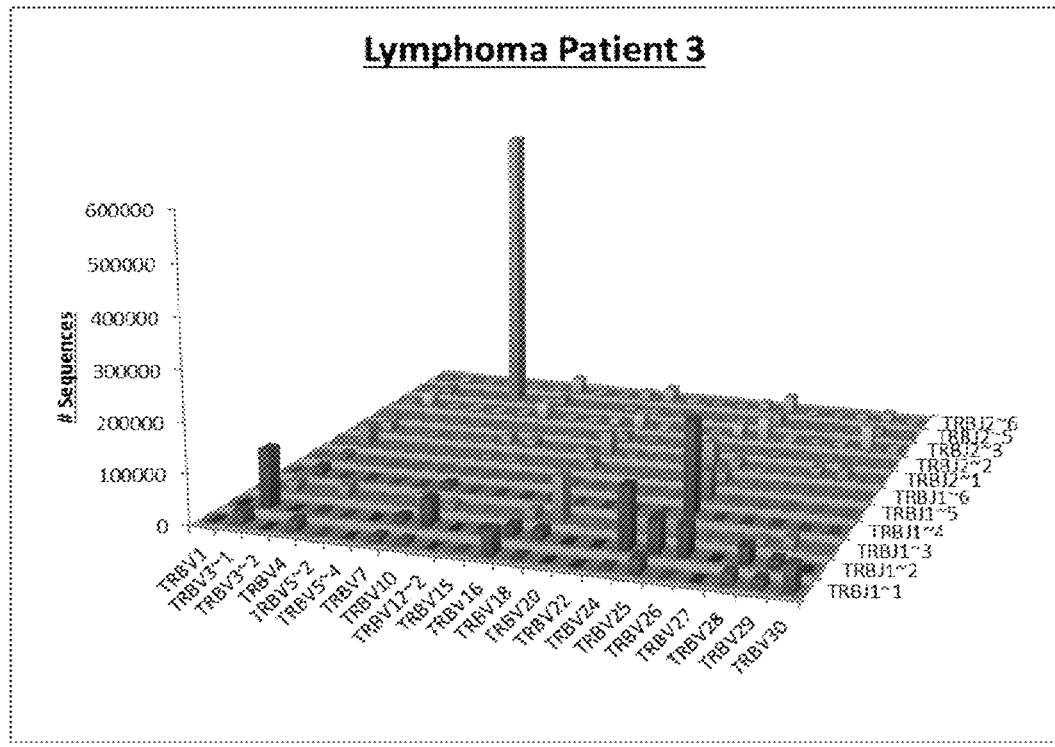
Figure 4D:
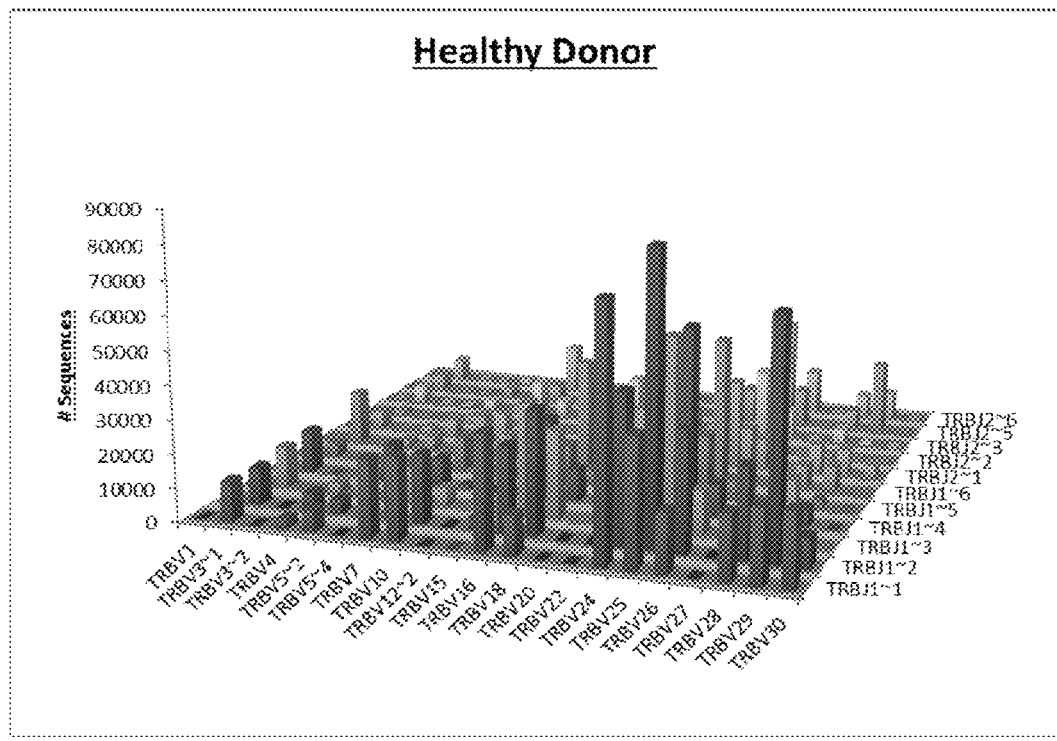

As shown in FIG. 3, when expressed as a percentage of the sequences encoding the same V-beta gene as the tumor clones, the dominance of the tumor clone becomes even more apparent with 92.2%, 63.1%, and 89.5% clonal dominance respectively. For example in lymphoma patient #1 there were 3927 unique TCR clones that utilized the TRBV25 gene with a cumulative frequencies of 1,796,486. The dominant tumor clone appeared 1,656,218 times and the remaining 3926 non-dominant TRBV25+ clones cumulatively appeared only 140,268 times. This indicates that only 7.8% of the TRBV25+ T cells were remaining healthy non-tumor cells in this patient.

FIGS. 4(A)-(D) show the landscape of the frequency profiles of all of the TCRs that share the same V-gene and J-gene for all four dogs. The presence of the tumor drastically alters the repertoire landscape, and potentially supplants the normal TCR repertoire. Each bar in this 3-D chart represents the sum of all of the TCR sequences that bear the same V-gene and J-gene segment within the patient sample. A veterinarian can use this chart to quickly scan the landscape of the TCR repertoire for global anomalies, that may indicate the presence of a lymphoma or leukemia. The landcape and clonal dominance plots in this canine high-throughput TCR sequencing protocol provide a diagnostic tool that can reliably distinguish between lymphoma and leukamia (typically mono-clonal) and other lympho-proliferative disorders like infection, auto-immune syndromes, etc (typically poly-clonal).

Example 3: Diversity Index Shannon's Entropy (H)

To confirm that the high frequency tumor clone actually led to a reduction in the diversity of the healthy T cell population, the Shannon's Entropy Diversity Index was calculated for each sample.

Shannon's Entropy (H), which takes into account species richness and the frequency distribution (or evenness) of the species in the sample, is calculated using Equation I:

$$H = -\sum_{i=1}^{S} p_i \log(p_i) \quad (I)$$

where i is a given TCR clone in the sample and pi is the proportion of the sample composed of by clone i, and S is the number of unique clones in the sample. Entropy is highest when there are many different clones and when the highest frequency clones are not particularly dominant.

Figure 5:
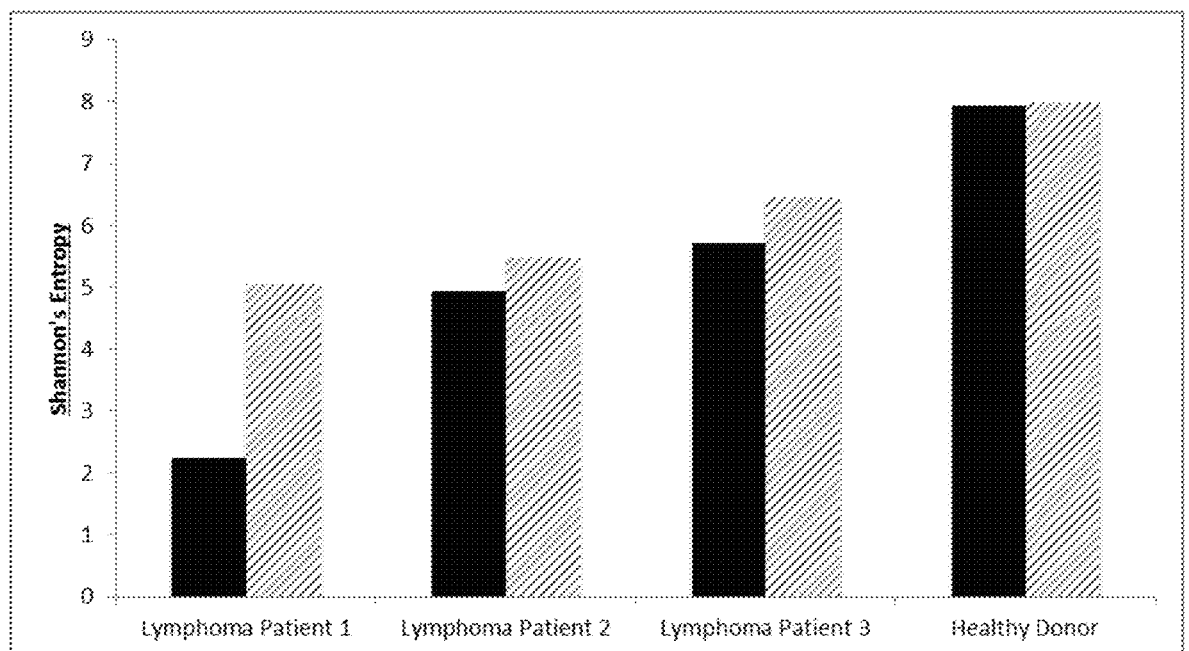
FIG. 5 is a bar graph showing the change in Shannon's Diversity occasioned by the presence of a high-frequency tumor-bearing TCR clonotype on the remaining healthy repertoire of V- and J-genes. The black bars show the diversity (Shannon's Entropy) of each sample. The diversity is severely reduced in the lymphoma patients. The grey bars show the diversity of the "healthy" portion of the repertoire (omitting the high frequency clone).

The presence of the high frequency tumor clone was shown to drive down the Entropy value of the tumor samples, relative to the healthy donor. In addition, the presence of the tumor was shown to also proportionally reduce the number of healthy clones in the tumor patient, which drives down the patient's Shannon Diversity Index. Shannon's Entropy values for each sample are shown in FIG. 5.

To determine whether the presence of the dominant clone alters the diversity of the remaining TCR repertoire, Shannon's Entropy was also re-calculated for the "healthy" portion of the repertoire (excluding the high frequency clone from each sample), and the diversity was still hampered only within the lymphoma patient samples, suggesting there was an actual loss of "healthy" TCRs. The Chao-1 index was also calculated, which is a species richness index that estimates the total number of species in the tissue that the TCR sequences were sampled from. The Chao-1 index estimated that the healthy donor tissue had a 266% higher clonal diversity than the mean of the lymphoma patients, thus supporting the conclusion that tumor clones supersede the healthy T cells in these patients.

Example 4: Clinical Clonotype Abundance Threshold

In order to confirm that a sequence abundance threshold of ≥5% may be used to identify high-frequency clones as tumors when normalized per million sequences in the sample, the abundance of each clone per 1 million sequences in the respective dataset was calculated.

Figure 6:
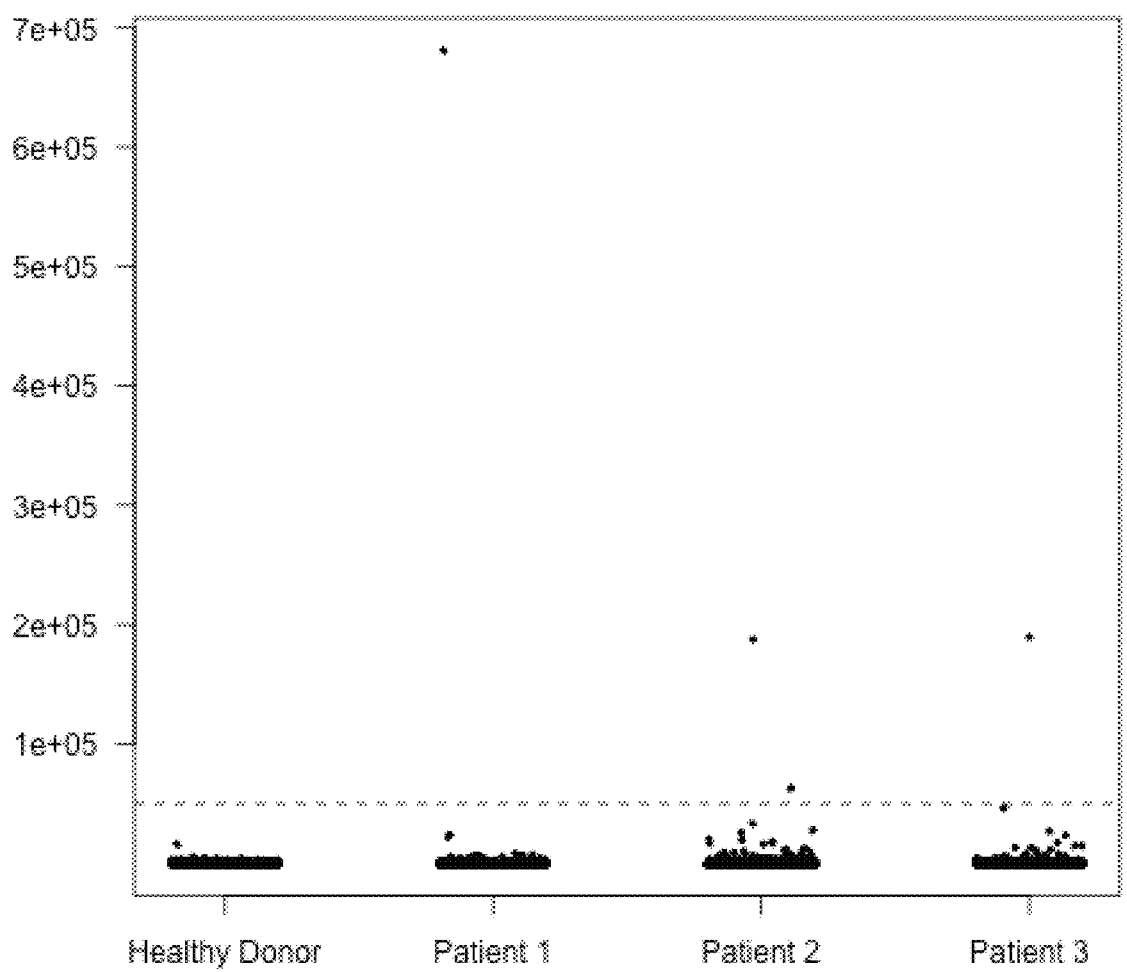
FIG. 6 is a scatter plot showing that the high frequency TCRs within the lymphoma patients (Patients 1-3) exceed the dominance threshold. TCR clone frequency threshold per 1 million sequences of ≥5% is indicated by the dashed line.
Figure 7:
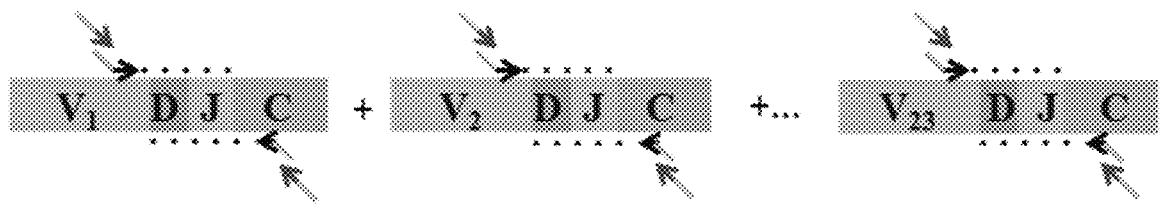
FIG. 7 is a schematic illustrating the creation of primers to amplify the known functional canine TCR Vβ genes for molecular tagging in cTCRβ PCR.

As shown in FIG. 6, the healthy donor is clearly distinguishable from the lymphoma patients by this criterion. For all lymphoma cases a clear clonal expansion that dominates the TCR repertoire and exceeds this lymphoma threshold was identifiable. The dominant sequence in the three lymphoma cases were 13.61×, 3.75×, and 3.79× above the clinical threshold, whereas the peak frequency clone in the healthy donor fell 3.12× below the threshold, indicating that this benchmark may also be appropriate in identifying lymphoma cases in canine patients.

The various embodiments of the invention described above can be combined to provide further embodiments of the invention. All of the references and products referred to in this application are incorporated herein by reference in their entirety. Embodiments of the invention can be modified, if necessary to employ concepts of the references and/or products referred to in this application to provide yet further embodiments of the invention.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are limited by the disclosure.

What is claimed is:

1. A method comprising the steps of:
   (i) creating a TCRβ(T cell receptor β chain) DNA library using a biological sample obtained from a subject,
   (ii) assessing the frequency of each TCR clonotype;
   (iii) identifying a tumor-bearing TCR clonotype using one or more clonal abundance indices;
   (iv) comparing the frequency of the tumor-bearing TCR clonotype to an abundance threshold criterion derived from the frequency of the dominant clone in samples obtained from a plurality of subjects diagnosed as not having T-cell lymphoma or leukemia; and
   (v) identifying the subject as having T-cell lymphoma or leukemia when the frequency is above the abundance threshold criterion or identifying the subject as not having T-cell lymphoma or leukemia when the frequency is below the abundance threshold criterion,
   wherein the creation of the TCRβ DNA library comprises the steps of:
   (a) isolating RNA from the biological sample:
   (b) generating DNA product via reverse transcription of the isolated RNA and amplifying the resultant DNA product:
   (c) analyzing the amplified DNA product; and
   (d) sequencing of the amplified DNA product; and
   wherein the step of amplification of the resultant DNA product comprises incorporating a randomized molecular tag that is contiguous with an adaptor sequence into each molecule of input TCR, and wherein the incorporation of the randomized molecular tag that is contiguous with the adaptor sequence comprises the step of annealing each molecule of input TCR mRNA to a primer having the randomized molecular tag that is contiguous with the adaptor sequence.

2. The method of claim 1, wherein the biological sample and samples are selected from the group consisting of lymph node tissue, peripheral blood lymphocytes, bone marrow, gut associated lymphoid tissue, other tissue having a malignant lymphoid lesion, and a combination thereof.

3. The method of claim 1, wherein the steps of reverse transcription and amplification are performed using RT-PCR.

4. The method of claim 1, wherein the step of sequencing of the amplified DNA product is performed using high-throughput sequencing.

5. The method of claim 1 wherein the abundance threshold criterion is greater than or equal to 1%, 2%, 3%, 4%, 5%, 10%, or 15%.

6. The method of claim 1, wherein the abundance threshold criterion is greater than or equal to 5%.

7. The method of claim 1, wherein the primer has a nucleic acid sequence comprising one or more of SEQ ID NO. 5 through SEQ ID NO. 26.

8. The method of claim 1, wherein the primer has a nucleic acid sequence comprising one or more of SEQ ID NO. 17 through SEQ ID NO. 26.

9. The method of claim 1, wherein the subject is canine.

10. The method of claim 1, wherein the randomized molecular tag is a random sequence of contiguous nucleotides selected from A, C, T or G, and is less than 10 nucleotides in length.

11. The method of claim 1, wherein the adaptor sequence comprises at least one of SEQ ID NO: 49 through SEQ ID NO: 56.

12. A method comprising the steps of:
   (i) creating a TCRβ (T cell receptor β chain) DNA library using a biological sample obtained from a subject,
   (ii) assessing the frequency of each TCR clonotype;
   (iii) identifying a tumor-bearing TCR clonotype using one or more clonal abundance indices;
   (iv) comparing the frequency of the tumor-bearing TCR clonotype to an abundance threshold criterion derived from the frequency of the dominant clone in samples obtained from a plurality of subjects diagnosed as not having T-cell lymphoma or leukemia; and
   (v) identifying the subject as having an increased likelihood of T-cell lymphoma or leukemia recurrence when the frequency is above the abundance threshold criterion or identifying the subject as having a decreased likelihood of recurrence when the frequency is below the abundance threshold criterion,
   wherein the creation of the TCRβ DNA library comprises the steps of:
   (a) isolating RNA from the biological sample;
   (b) generating DNA product via reverse transcription of the isolated RNA and amplifying the resultant DNA product;
   (c) analyzing the amplified DNA product; and
   (d) sequencing of the amplified DNA product; and
   wherein the step of amplification of the resultant DNA product comprises incorporating a randomized molecular tag that is contiguous with an adaptor sequence into each molecule of input TCR, and wherein the incorporation of the randomized molecular tag that is contiguous with the adaptor sequence comprises the step of annealing each molecule of input TCR mRNA to a primer having the randomized molecular tag that is contiguous with the adaptor sequence.

13. The method of claim 11, wherein the biological sample and samples are selected from the group consisting of lymph node tissue, peripheral blood lymphocytes, bone marrow, gut associated lymphoid tissue, other tissue having a malignant lymphoid lesion, and a combination thereof.

14. The method of claim 12, wherein the steps of reverse transcription and amplification are performed concurrently using RT-PCR.

15. The method of claim 12, wherein the step of sequencing of the amplified DNA product is performed using high-throughput sequencing.

16. The method of claim 12, wherein the abundance threshold criterion is greater than or equal to 1%, 2%, 3%, 4%, 5%, 10%, or 15%.

17. The method of claim 12, wherein the abundance threshold criterion is greater than or equal to 5%.

18. The method of claim 12, wherein the primer has a nucleic acid sequence comprising one or more of SEQ ID NO. 5 through SEQ ID NO. 26.

19. The method of claim 12, wherein the primer has a nucleic acid sequence comprising one or more of SEQ ID NO. 17 through SEQ ID NO. 26.

20. The method of claim 12, wherein the subject is canine.

21. The method of claim 12, wherein the randomized molecular tag is a random sequence of contiguous nucleotides selected from A, C, T or G, and is less than 10 nucleotides in length.

22. The method of claim 12, wherein the adaptor sequence comprises at least one of SEQ ID NO: 49 through SEQ ID NO: 56.

23. A kit for diagnosing a subject suspected to be suffering from or susceptible to recurring T-cell lymphoma or leukemia, said kit comprising at least one forward primer and at least one reverse primer, the forward primer and the reverse primer each has a nucleic acid sequence comprising one or more of SEQ ID NO. 5 through SEQ ID NO. 26, together with instructions for carrying out the method of claim 1.

24. A kit for determining the risk of a subject for T-cell lymphoma or leukemia recurrence after transient remission comprising at least one forward primer and at least one reverse primer, the forward primer and the reverse primer each has a nucleic acid sequence comprising one or more of SEQ ID NO. 17 through SEQ ID NO. 26, together with instructions for carrying out the method of claim 12.

25. An oligonucleotide primer composition comprising at least 15 and not more than 100 contiguous nucleotides of a V or C region encoding gene sequence for TCRI3, which is contiguous with a molecular tag that is contiguous with an adaptor sequence, wherein the composition comprises an oligonucleotide having a sequence selected from the group consisting of SEQ ID NO. 5 through SEQ ID NO. 26.

* * * * *